(12) United States Patent
Leung et al.

(10) Patent No.: US 8,609,817 B2
(45) Date of Patent: Dec. 17, 2013

(54) ANTI-HEPCIDIN-25 SELECTIVE ANTIBODIES AND USES THEREOF

(75) Inventors: Donmienne Doen Mun Leung, San Diego, CA (US); Peng Luan, Fishers, IN (US); Ying Tang, San Diego, CA (US); Derrick Ryan Witcher, Fishers, IN (US); Pia Pauliina Yachi, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 252 days.

(21) Appl. No.: 13/055,201

(22) PCT Filed: Jul. 29, 2009

(86) PCT No.: PCT/US2009/052044
§ 371 (c)(1),
(2), (4) Date: Jan. 21, 2011

(87) PCT Pub. No.: WO2010/017070
PCT Pub. Date: Feb. 11, 2010

(65) Prior Publication Data
US 2011/0189190 A1   Aug. 4, 2011

Related U.S. Application Data

(60) Provisional application No. 61/086,557, filed on Aug. 6, 2008.

(51) Int. Cl.
| C07K 16/00 | (2006.01) |
| C12P 21/08 | (2006.01) |
| G01N 33/53 | (2006.01) |
| A61K 39/395 | (2006.01) |
| A61K 39/40 | (2006.01) |
| C07K 1/00 | (2006.01) |

(52) U.S. Cl.
USPC ............ 530/387.1; 530/387.3; 530/388.1; 530/388.23; 530/388.24; 530/388.25; 530/391.1; 435/7.1; 435/810; 424/130.1; 424/132.1; 424/133.1; 424/141.1; 424/145.1; 424/158.1

(58) Field of Classification Search
None
See application file for complete search history.

(56) References Cited

U.S. PATENT DOCUMENTS

| 7,320,894 B2 | 1/2008 | Kulaksiz et al. |
| 7,820,163 B2 | 10/2010 | Leung et al. |
| 2004/0096987 A1 | 5/2004 | Geacintov et al. |
| 2005/0037971 A1 | 2/2005 | Nicolas et al. |
| 2006/0019339 A1 | 1/2006 | Lauth et al. |
| 2007/0224186 A1 | 9/2007 | Kulaksiz et al. |
| 2011/0027261 A1 | 2/2011 | Leung et al. |

FOREIGN PATENT DOCUMENTS

| CN | 1173737 C | 11/2004 |
| WO | 00/73454 A1 | 12/2000 |
| WO | 01/16317 A2 | 3/2001 |
| WO | 2004/058044 A2 | 7/2004 |
| WO | 2005/033327 A2 | 4/2005 |
| WO | 2006/099126 A2 | 9/2006 |
| WO | 2008/089795 A1 | 7/2008 |
| WO | 2008/097461 A2 | 8/2008 |
| WO | 2009/027752 A2 | 3/2009 |
| WO | 2009/044284 A1 | 4/2009 |
| WO | 2009/139822 A1 | 11/2009 |

OTHER PUBLICATIONS

Colman et al. Research in Immunology, 1994; 145(1): 33-36.*
Pietrangelo. Journal of Hepatology 2011. vol. 54 pp. 173-181.*
Kemna, E.H., et al., Haematologica, "Hepcidin: From Discovery to Differential Diagnosis," 93(1):90-97 (2008).
Gutierrez, J.A., et al., BioTechniques, "Quantitative Determination of Peptides Using Matrix-Assisted Laser Desorption/Ionization Time-Of-Flight Mass Spectrometry," 38:S13-S17 (2005).
Murphy, et al., Blood, "Quantitation of Hepcidin From Human and Mouse Serum Using Liquid Chromatography Tandem Mass Spectrometry," 110:1048-1054 (2007).
Kemna, E.H., et al., Clinical Chemistry, "Mass Spectrometry-Based Hepcidin Measurement in Serum and Urine: Analytical Aspects and Clinical Implications," 53:620-628 (2007).
Tomosugi, Naohisa, et al., Blood, Amercian Society of Hematology, "Detection of Serum Hepcidin in Renal Failure and Inflammation by using Protein Chip System," 108(4):1381-1387 (2006).
Koliaraki, Vailike, et al., Plos One, "A Novel Immunological Assay for Hepcidin Quantification in Human Serum," 4 (2):e4581 (2009).
Alpha Diagnostic International, Product Specification Sheet, Catalog # HEPC11-S, HEPC11-A, HEPC11-P, www.4adi.com (2008).
Alpha Diagnostic International, Product Specification Sheet, Catalog # HEPC12-S, HEPC12-A, HEPC12-P, www.4adi.com (2008).
Alpha Diagnostic International, Product Specification Sheet, Catalog # HEPC13-S, HEPC13-A, HEPC13-P, www.4adi.com.
DRG Hepcidin Prohormone ELISA (EIA-4644) corp@drg-international.com, pp. 1-10 (2007).
Kemna, Erwin H.J.M., et al., "Measuring Serum Hepcidin Concentrations," Nature Clinical Practice Gastroenterology & Hepatology, 2, E1 (2005).
Nemeth, Elizabeta, et al., "Hepcidin, A Putative Mediator of Anemia of Inflammation, Is a Type II Acute-Phase Protein," Blood, vol. 101(7) (2003).
Nicolas, Gael, et al., "Lack of Hepcidin Gene Expression and Sever Tissue Iron Overload in Upstream Stimulatory Factor 2 (USF2) Knockout Mice," PNAS, vol. 98(15), pp. 8780-8785 (2001).

(Continued)

Primary Examiner — Chun Dahle
(74) Attorney, Agent, or Firm — Robert L. Sharp

(57) ABSTRACT

Monoclonal antibodies are provided that bind to the N-terminus of human hepcidin-25 and are characterized as having high affinity and selectivity for the polypeptide. The antibodies of the invention are useful for increasing serum iron levels, reticulocyte count, red blood cell count, hemoglobin, and/or hematocrit in a human and for the treatment of various disorders, such as anemia, in a human subject. The antibodies of the invention are also useful as analytical tools, such as in sandwich ELISA.

17 Claims, 5 Drawing Sheets

(56) References Cited

OTHER PUBLICATIONS

Roe, Mark A., et al., "Serum Prohepcidin Concentration: No Association With Iron Absorption in Healthy Men; and No Relationship With Iron Status in Men Carrying HFE Mutations, Hereditary Haemochromatosis Patients Undergoing Phlebotomy Treatment, or Pregnant Women," British Journal of Nutrition, vol. 97, pp. 544-549 (2007).

Valore, Erika, et al., "Posttransitional Processing of Hepcidin in Human Hepatocytes is Mediated by the Prohormone Convertase Furin," Blood Cells, Molecules, and Diseases, 40, pp. 132-138 (2008).

* cited by examiner

SEQUENCE LISTING

<160> NUMBER OF SEQ ID NOS: 90

<210> SEQ ID NO 1
<211> LENGTH: 25
<212> TYPE: PRT
<213> ORGANISM: Homo sapiens

<400> SEQUENCE: 1

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 2
<211> LENGTH: 25
<212> TYPE: PRT
<213> ORGANISM: Rattus rattus

<400> SEQUENCE: 2

Asp Thr Asn Phe Pro Ile Cys Leu Phe Cys Cys Lys Cys Cys Lys Asn
1               5                   10                  15

Ser Ser Cys Gly Leu Cys Cys Ile Thr
            20                  25

<210> SEQ ID NO 3
<211> LENGTH: 25
<212> TYPE: PRT
<213> ORGANISM: Mus musculus

<400> SEQUENCE: 3

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 4
<211> LENGTH: 25
<212> TYPE: PRT
<213> ORGANISM: macaca sp.

<400> SEQUENCE: 4

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Asp Thr His Phe Pro Ile Cys
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

```
<220> FEATURE:
<221> NAME/KEY: MISC_FEATURE
<222> LOCATION: (6)..(6)
<223> OTHER INFORMATION: Xaa at position 6 is Val or Ala
<220> FEATURE:
<221> NAME/KEY: MISC_FEATURE
<222> LOCATION: (8)..(8)
<223> OTHER INFORMATION: Xaa at position 8 is Tyr or Ser

<400> SEQUENCE: 6

Ser Ala Ser Ser Ser Xaa Ser Xaa Met Tyr
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 is Asn or His

<400> SEQUENCE: 7

Leu Thr Ser Xaa Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa at position 6 is Asn, Gly, or Tyr

<400> SEQUENCE: 8

Gln Gln Trp Ser Ser Xaa Pro Pro Thr
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Ser Ala Ser Ser Ser Val Ser Tyr Met Tyr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Leu Thr Ser Asn Leu Ala Ser
1               5

<210> SEQ ID NO 11
<211> LENGTH: 9
<212> TYPE: PRT
<213> ORGANISM: Artificial Sequence
<220> FEATURE:
```

```
<223> OTHER INFORMATION: Synthetic Construct

<400> SEQUENCE: 11

Gln Gln Trp Ser Ser Asn Pro Pro Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Ser Ala Ser Ser Ser Ala Ser Tyr Met Tyr
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Leu Thr Ser His Leu Ala Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Gln Gln Trp Ser Ser Gly Pro Pro Thr
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Ser Ala Ser Ser Ser Val Ser Ser Met Tyr
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Gln Gln Trp Ser Ser Tyr Pro Pro Thr
1               5

<210> SEQ ID NO 17
<211> LENGTH: 16
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (9)..(9)
<223> OTHER INFORMATION: Xaa at position 9 is Ser, Arg, or Pro

<400> SEQUENCE: 17

Lys Ser Ser Gln Ser Leu Leu Tyr Xaa Asn Gly Lys Thr Tyr Leu Thr
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa at position 7 is Ser or Pro

<400> SEQUENCE: 18

Leu Val Ser Lys Leu Asp Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Val, His, Ile or Phe
<220> FEATURE:
<221> NAME/KEY: MISC_FEATURE
<222> LOCATION: (9)..(9)
<223> OTHER INFORMATION: Xaa at position 9 is Thr or Val

<400> SEQUENCE: 19

Xaa Gln Gly Ser His Phe Pro Trp Xaa
1               5

<210> SEQ ID NO 20
<211> LENGTH: 16
<212> TYPE: PRT
<213> ORGANISM: Artificial Sequence
<220> FEATURE:
<223> OTHER INFORMATION: Synthetic Construct

<400> SEQUENCE: 20

Lys Ser Ser Gln Ser Leu Leu Tyr Ser Asn Gly Lys Thr Tyr Leu Thr
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Leu Val Ser Lys Leu Asp Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 22

Val Gln Gly Ser His Phe Pro Trp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

His Gln Gly Ser His Phe Pro Trp Thr
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic Construct

<400> SEQUENCE: 24

Lys Ser Ser Gln Ser Leu Leu Tyr Arg Asn Gly Lys Thr Tyr Leu Thr
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Leu Val Ser Lys Leu Asp Pro
1               5

<210> SEQ ID NO 26
<211> LENGTH: 16
<212> TYPE: PRT
<213> ORGANISM: Artificial Sequence
<220> FEATURE:
<223> OTHER INFORMATION: Synthetic Construct

<400> SEQUENCE: 26

Lys Ser Ser Gln Ser Leu Leu Tyr Pro Asn Gly Lys Thr Tyr Leu Thr
1               5                   10                  15

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Ile Gln Gly Ser His Phe Pro Trp Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

```
Phe Gln Gly Ser His Phe Pro Trp Val
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Phe, Tyr or Leu
<220> FEATURE:
<221> NAME/KEY: MISC_FEATURE
<222> LOCATION: (5)..(5)
<223> OTHER INFORMATION: Xaa at position 5 is Ser or Asn
<220> FEATURE:
<221> NAME/KEY: MISC_FEATURE
<222> LOCATION: (6)..(6)
<223> OTHER INFORMATION: Xaa at position 6 is Thr or Ser
<220> FEATURE:
<221> NAME/KEY: MISC_FEATURE
<222> LOCATION: (7)..(7)
<223> OTHER INFORMATION: Xaa at position 7 is Tyr or Pro
<220> FEATURE:
<221> NAME/KEY: MISC_FEATURE
<222> LOCATION: (9)..(9)
<223> OTHER INFORMATION: Xaa at position 9 is Ile or Phe
<220> FEATURE:
<221> NAME/KEY: MISC_FEATURE
<222> LOCATION: (11)..(11)
<223> OTHER INFORMATION: Xaa at position 11 is Val or Ile

<400> SEQUENCE: 29

Gly Xaa Ser Leu Xaa Xaa Xaa Gly Xaa Gly Xaa Gly
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa at position 6 is Asp or Gly
<220> FEATURE:
<221> NAME/KEY: MISC_FEATURE
<222> LOCATION: (7)..(7)
<223> OTHER INFORMATION: Xaa at position 7 is Ala or Asn
<220> FEATURE:
<221> NAME/KEY: MISC_FEATURE
<222> LOCATION: (9)..(9)
<223> OTHER INFORMATION: Xaa at position 9 is Ser or Tyr
<220> FEATURE:
<221> NAME/KEY: MISC_FEATURE
<222> LOCATION: (13)..(13)
<223> OTHER INFORMATION: Xaa at position 13 is Ala or Thr

<400> SEQUENCE: 30

His Ile Trp Trp Asn Xaa Xaa Lys Xaa Tyr Asn Thr Xaa Leu Lys Ser
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
```

```
<223> OTHER INFORMATION: Xaa at position 2 is Gly or His
<220> FEATURE:
<221> NAME/KEY: MISC_FEATURE
<222> LOCATION: (6)..(6)
<223> OTHER INFORMATION: Xaa at position 6 is Ser or Asn
<220> FEATURE:
<221> NAME/KEY: MISC_FEATURE
<222> LOCATION: (7)..(7)
<223> OTHER INFORMATION: Xaa at position 7 is Thr or Ser
<220> FEATURE:
<221> NAME/KEY: MISC_FEATURE
<222> LOCATION: (8)..(8)
<223> OTHER INFORMATION: Xaa at position 8 is Ser, Ala or Tyr

<400> SEQUENCE: 31

Ile Xaa Tyr Tyr Gly Xaa Xaa Xaa Gly Phe Ala Tyr
1               5                  10

<210> SEQ ID NO 32
<211> LENGTH: 12
<212> TYPE: PRT
<213> ORGANISM: Artificial Sequence
<220> FEATURE:
<223> OTHER INFORMATION: Synthetic Construct

<400> SEQUENCE: 32

Gly Phe Ser Leu Ser Thr Tyr Gly Ile Gly Val Gly
1               5                  10

<210> SEQ ID NO 33
<211> LENGTH: 16
<212> TYPE: PRT
<213> ORGANISM: Artificial Sequence
<220> FEATURE:
<223> OTHER INFORMATION: Synthetic Construct

<400> SEQUENCE: 33

His Ile Trp Trp Asn Asp Asn Lys Ser Tyr Asn Thr Ala Leu Lys Ser
1               5                  10                  15

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct

<400> SEQUENCE: 34

Ile Gly Tyr Tyr Gly Ser Thr Ser Gly Phe Ala Tyr
1               5                  10

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct

<400> SEQUENCE: 35

Gly Tyr Ser Leu Ser Thr Pro Gly Ile Gly Val Gly
1               5                  10

<210> SEQ ID NO 36
<211> LENGTH: 16
<212> TYPE: PRT
<213> ORGANISM: Artificial Sequence
<220> FEATURE:
<223> OTHER INFORMATION: Synthetic Construct

<400> SEQUENCE: 36
```

His Ile Trp Trp Asn Asp Ala Lys Ser Tyr Asn Thr Ala Leu Lys Ser
1               5                   10                  15

<210> SEQ ID NO 37
<211> LENGTH: 12
<212> TYPE: PRT
<213> ORGANISM: Artificial Sequence
<220> FEATURE:
<223> OTHER INFORMATION: Synthetic Construct

<400> SEQUENCE: 37

Ile Gly Tyr Tyr Gly Ser Thr Ala Gly Phe Ala Tyr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

Gly Leu Ser Leu Ser Thr Pro Gly Ile Gly Val Gly
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic Construct

<400> SEQUENCE: 39

Gly Phe Ser Leu Asn Ser Tyr Gly Phe Gly Ile Gly
1               5                   10

<210> SEQ ID NO 40
<211> LENGTH: 16
<212> TYPE: PRT
<213> ORGANISM: Artificial Sequence
<220> FEATURE:
<223> OTHER INFORMATION: Synthetic Construct

<400> SEQUENCE: 40

His Ile Trp Trp Asn Gly Asn Lys Tyr Tyr Asn Thr Thr Leu Lys Ser
1               5                   10                  15

<210> SEQ ID NO 41
<211> LENGTH: 12
<212> TYPE: PRT
<213> ORGANISM: Artificial Sequence
<220> FEATURE:
<223> OTHER INFORMATION: Synthetic Construct

<400> SEQUENCE: 41

Ile His Tyr Tyr Gly Asn Ser Tyr Gly Phe Ala Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Phe Ala Phe Ser Ser Tyr Asp Met Ser

<210> SEQ ID NO 43
<211> LENGTH: 17
<212> TYPE: PRT
<213> ORGANISM: Artificial Sequence
<220> FEATURE:
<223> OTHER INFORMATION: Synthetic Construct

<400> SEQUENCE: 43

Thr Ile Ile Ser Gly Gly Thr Tyr Thr Tyr Tyr Pro Asp Ser Val Lys
1               5                   10                  15
Gly

<210> SEQ ID NO 44
<211> LENGTH: 5
<212> TYPE: PRT
<213> ORGANISM: Artificial Sequence
<220> FEATURE:
<223> OTHER INFORMATION: Synthetic Construct

<400> SEQUENCE: 44

Asp Gly Tyr Ile His
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Ser Ala Ser Pro Ser Val Ser Tyr Met Tyr
1               5                   10

<210> SEQ ID NO 46
<211> LENGTH: 106
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Asp or Gln
<220> FEATURE:
<221> NAME/KEY: MISC_FEATURE
<222> LOCATION: (3)..(3)
<223> OTHER INFORMATION: Xaa at position 3 is Leu or Gln
<220> FEATURE:
<221> NAME/KEY: MISC_FEATURE
<222> LOCATION: (4)..(4)
<223> OTHER INFORMATION: Xaa at position 4 is Leu or Met
<220> FEATURE:
<221> NAME/KEY: MISC_FEATURE
<222> LOCATION: (5)..(5)
<223> OTHER INFORMATION: Xaa at position 5 is Thr or Asn
<220> FEATURE:
<221> NAME/KEY: MISC_FEATURE
<222> LOCATION: (27)..(27)
<223> OTHER INFORMATION: Xaa at position 27 is Ser or Pro
<220> FEATURE:
<221> NAME/KEY: MISC_FEATURE
<222> LOCATION: (29)..(29)
<223> OTHER INFORMATION: Xaa at position 29 is Val or Ala
<220> FEATURE:
<221> NAME/KEY: MISC_FEATURE
<222> LOCATION: (31)..(31)
<223> OTHER INFORMATION: Xaa at position 31 is Tyr or Ser
<220> FEATURE:
<221> NAME/KEY: MISC_FEATURE

```
<222> LOCATION: (52)..(52)
<223> OTHER INFORMATION: Xaa at position 52 is Asn or His
<220> FEATURE:
<221> NAME/KEY: MISC_FEATURE
<222> LOCATION: (59)..(59)
<223> OTHER INFORMATION: Xaa at position 59 is Ala or Pro
<220> FEATURE:
<221> NAME/KEY: MISC_FEATURE
<222> LOCATION: (76)..(76)
<223> OTHER INFORMATION: Xaa at position 76 is Ser or Asn
<220> FEATURE:
<221> NAME/KEY: MISC_FEATURE
<222> LOCATION: (93)..(93)
<223> OTHER INFORMATION: Xaa at position 93 is Asn, Tyr or Gly

<400> SEQUENCE: 46

Xaa Ile Xaa Xaa Xaa Gln Ser Pro Ala Leu Met Ser Ala Ser Pro Gly
1               5                   10                  15

Glu Lys Val Thr Met Thr Cys Ser Ala Ser Xaa Ser Xaa Ser Xaa Met
            20                  25                  30

Tyr Trp Tyr Gln Gln Lys Pro Arg Ser Ser Pro Lys Pro Trp Ile Tyr
        35                  40                  45

Leu Thr Ser Xaa Leu Ala Ser Gly Val Pro Xaa Arg Phe Ser Gly Ser
    50                  55                  60

Gly Ser Gly Thr Ser Tyr Ser Leu Thr Ile Ser Xaa Met Glu Ala Glu
65                  70                  75                  80

Asp Ala Ala Thr Tyr Tyr Cys Gln Gln Trp Ser Ser Xaa Pro Pro Thr
                85                  90                  95

Phe Gly Gly Gly Thr Lys Leu Glu Ile Lys
            100                 105

<210> SEQ ID NO 47
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Glu or Gln
<220> FEATURE:
<221> NAME/KEY: MISC_FEATURE
<222> LOCATION: (3)..(3)
<223> OTHER INFORMATION: Xaa at position 3 is Lys or Gln
<220> FEATURE:
<221> NAME/KEY: MISC_FEATURE
<222> LOCATION: (5)..(5)
<223> OTHER INFORMATION: Xaa at position 5 is Lys or Val
<220> FEATURE:
<221> NAME/KEY: MISC_FEATURE
<222> LOCATION: (6)..(6)
<223> OTHER INFORMATION: Xaa at position 6 is Gln or Glu
<220> FEATURE:
<221> NAME/KEY: MISC_FEATURE
<222> LOCATION: (27)..(27)
<223> OTHER INFORMATION: Xaa at position 27 is Phe, Tyr or Leu
<220> FEATURE:
<221> NAME/KEY: MISC_FEATURE
<222> LOCATION: (30)..(30)
<223> OTHER INFORMATION: Xaa at position 30 is Ser or Asn
<220> FEATURE:
<221> NAME/KEY: MISC_FEATURE
<222> LOCATION: (31)..(31)
<223> OTHER INFORMATION: Xaa at position 31 is Thr or Ser
<220> FEATURE:
<221> NAME/KEY: MISC_FEATURE
<222> LOCATION: (32)..(32)
<223> OTHER INFORMATION: Xaa at position 32 is Tyr or Pro
<220> FEATURE:
<221> NAME/KEY: MISC_FEATURE
<222> LOCATION: (34)..(34)
```

-continued

```
<223> OTHER INFORMATION: Xaa at position 34 is Ile or Phe
<220> FEATURE:
<221> NAME/KEY: MISC_FEATURE
<222> LOCATION: (36)..(36)
<223> OTHER INFORMATION: Xaa at position 36 is Val or Ile
<220> FEATURE:
<221> NAME/KEY: MISC_FEATURE
<222> LOCATION: (43)..(43)
<223> OTHER INFORMATION: Xaa at position 43 is Ala or Ser
<220> FEATURE:
<221> NAME/KEY: MISC_FEATURE
<222> LOCATION: (51)..(51)
<223> OTHER INFORMATION: Xaa at position 51 is Ala or Thr
<220> FEATURE:
<221> NAME/KEY: MISC_FEATURE
<222> LOCATION: (57)..(57)
<223> OTHER INFORMATION: Xaa at position 57 is Asp or Gly
<220> FEATURE:
<221> NAME/KEY: MISC_FEATURE
<222> LOCATION: (58)..(58)
<223> OTHER INFORMATION: Xaa at position 58 is Asn or Ala
<220> FEATURE:
<221> NAME/KEY: MISC_FEATURE
<222> LOCATION: (60)..(60)
<223> OTHER INFORMATION: Xaa at position 60 is Ser or Tyr
<220> FEATURE:
<221> NAME/KEY: MISC_FEATURE
<222> LOCATION: (64)..(64)
<223> OTHER INFORMATION: Xaa at position 64 is Ala or Thr
<220> FEATURE:
<221> NAME/KEY: MISC_FEATURE
<222> LOCATION: (87)..(87)
<223> OTHER INFORMATION: Xaa at position 87 is Val or Leu
<220> FEATURE:
<221> NAME/KEY: MISC_FEATURE
<222> LOCATION: (89)..(89)
<223> OTHER INFORMATION: Xaa at position 89 is Thr or Ala
<220> FEATURE:
<221> NAME/KEY: MISC_FEATURE
<222> LOCATION: (90)..(90)
<223> OTHER INFORMATION: Xaa at position 90 is His or Asp
<220> FEATURE:
<221> NAME/KEY: MISC_FEATURE
<222> LOCATION: (97)..(97)
<223> OTHER INFORMATION: Xaa at position 97 is Val or Ala
<220> FEATURE:
<221> NAME/KEY: MISC_FEATURE
<222> LOCATION: (98)..(98)
<223> OTHER INFORMATION: Xaa at position 98 is Leu or Val
<220> FEATURE:
<221> NAME/KEY: MISC_FEATURE
<222> LOCATION: (100)..(100)
<223> OTHER INFORMATION: Xaa at position 100 is Gly or His
<220> FEATURE:
<221> NAME/KEY: MISC_FEATURE
<222> LOCATION: (104)..(104)
<223> OTHER INFORMATION: Xaa at position 104 is Ser or Asn
<220> FEATURE:
<221> NAME/KEY: MISC_FEATURE
<222> LOCATION: (105)..(105)
<223> OTHER INFORMATION: Xaa at position 105 is Thr or Ser
<220> FEATURE:
<221> NAME/KEY: MISC_FEATURE
<222> LOCATION: (106)..(106)
<223> OTHER INFORMATION: Xaa at position 106 is Ser, Ala or Tyr

<400> SEQUENCE: 47

Xaa Val Xaa Leu Xaa Xaa Ser Gly Pro Gly Ile Leu Gln Pro Ser Gln
 1               5                  10                  15

Thr Leu Ser Leu Thr Cys Ser Phe Ser Gly Xaa Ser Leu Xaa Xaa Xaa
                20                  25                  30

Gly Xaa Gly Xaa Gly Trp Ile Arg Gln Pro Xaa Gly Lys Gly Leu Glu
            35                  40                  45

Trp Leu Xaa His Ile Trp Trp Asn Xaa Xaa Lys Xaa Tyr Asn Thr Xaa
        50                  55                  60
```

Leu Lys Ser Arg Leu Thr Ile Ser Lys Asp Thr Ser Asn Asn Gln Val
65                  70                  75                  80

Phe Leu Lys Ile Ala Ser Xaa Asp Xaa Xaa Thr Ala Thr Tyr Tyr Cys
                85                  90                  95

Xaa Xaa Ile Xaa Tyr Tyr Gly Xaa Xaa Xaa Gly Phe Ala Tyr Trp Gly
            100                 105                 110

Gln Gly Thr Leu Val Thr Val Ser Ala
            115                 120

<210> SEQ ID NO 48
<211> LENGTH: 106
<212> TYPE: PRT
<213> ORGANISM: Artificial Sequence
<220> FEATURE:
<223> OTHER INFORMATION: Synthetic Construct

<400> SEQUENCE: 48

Gln Ile Leu Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 49
<211> LENGTH: 122
<212> TYPE: PRT
<213> ORGANISM: Artificial Sequence
<220> FEATURE:
<223> OTHER INFORMATION: Synthetic Construct

<400> SEQUENCE: 49

Gln Val Gln Leu Lys Gln Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
                20                  25                  30

Gly Ile Gly Val Gly Trp Ile Arg Gln Pro Ala Gly Lys Gly Leu Glu
            35                  40                  45

Trp Leu Ala His Ile Trp Trp Asn Asp Asn Lys Ser Tyr Asn Thr Ala
        50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr His Thr Ala Thr Tyr Tyr
                85                  90                  95

Cys Val Val Ile Gly Tyr Tyr Gly Ser Thr Ser Gly Phe Ala Tyr Trp
            100                 105                 110

Gly Gln Gly Thr Leu Val Thr Val Ser Ala
            115                 120

<210> SEQ ID NO 50
<211> LENGTH: 106

```
<212> TYPE: PRT
<213> ORGANISM: Artificial Sequence
<220> FEATURE:
<223> OTHER INFORMATION: Synthetic Construct

<400> SEQUENCE: 50

Gln Ile Leu Leu Thr Gln Ser Pro Ala Leu Met Ser Ala Ser Pro Gly
1               5                   10                  15

Glu Lys Val Thr Met Thr Cys Ser Ala Ser Ser Ser Ala Ser Tyr Met
            20                  25                  30

Tyr Trp Tyr Gln Gln Lys Pro Arg Ser Ser Pro Lys Pro Trp Ile Tyr
        35                  40                  45

Leu Thr Ser His Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Gly Pro Pro Thr
                85                  90                  95

Phe Gly Gly Gly Thr Lys Leu Glu Ile Lys
            100                 105

<210> SEQ ID NO 51
<211> LENGTH: 122
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Lys Gln Ser Gly Pro Gly Ile Leu Gln Pro Ser Gln
1               5                   10                  15

Thr Leu Ser Leu Thr Cys Ser Phe Ser Gly Tyr Ser Leu Ser Thr Pro
            20                  25                  30

Gly Ile Gly Val Gly Trp Ile Arg Gln Pro Ala Gly Lys Gly Leu Glu
        35                  40                  45

Trp Leu Ala His Ile Trp Trp Asn Asp Ala Lys Ser Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Thr His Thr Ala Thr Tyr Tyr
                85                  90                  95

Cys Val Val Ile Gly Tyr Tyr Gly Ser Thr Ala Gly Phe Ala Tyr Trp
            100                 105                 110

Gly Gln Gly Thr Leu Val Thr Val Ser Ala
        115                 120

<210> SEQ ID NO 52
<211> LENGTH: 106
<212> TYPE: PRT
<213> ORGANISM: Artificial Sequence
<220> FEATURE:
<223> OTHER INFORMATION: Synthetic Construct

<400> SEQUENCE: 52

Gln Ile Leu Leu Thr Gln Ser Pro Ala Leu Met Ser Ala Ser Pro Gly
1               5                   10                  15

Glu Lys Val Thr Met Thr Cys Ser Ala Ser Pro Ser Val Ser Tyr Met
            20                  25                  30

Tyr Trp Tyr Gln Gln Lys Pro Arg Ser Ser Pro Lys Pro Trp Ile Tyr
        35                  40                  45
```

```
Leu Thr Ser His Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Gly Pro Pro Thr
                    85                  90                  95

Phe Gly Gly Gly Thr Lys Leu Glu Ile Lys
            100                 105

<210> SEQ ID NO 53
<211> LENGTH: 106
<212> TYPE: PRT
<213> ORGANISM: Artificial Sequence
<220> FEATURE:
<223> OTHER INFORMATION: Synthetic Construct

<400> SEQUENCE: 53

Gln Ile Leu Leu Thr Gln Ser Pro Ala Leu Met Ser Ala Ser Pro Gly
 1               5                  10                  15

Glu Lys Val Thr Met Thr Cys Ser Ala Ser Ser Ser Ala Ser Tyr Met
                20                  25                  30

Tyr Trp Tyr Gln Gln Lys Pro Arg Ser Ser Pro Lys Pro Trp Ile Tyr
            35                  40                  45

Leu Thr Ser His Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Gly Pro Pro Thr
                    85                  90                  95

Phe Gly Gly Gly Thr Lys Leu Glu Ile Lys
            100                 105

<210> SEQ ID NO 54
<211> LENGTH: 122
<212> TYPE: PRT
<213> ORGANISM: Artificial Sequence
<220> FEATURE:
<223> OTHER INFORMATION: Synthetic Construct

<400> SEQUENCE: 54

Gln Val Gln Leu Lys Gln Ser Gly Pro Gly Ile Leu Gln Pro Ser Gln
 1               5                  10                  15

Thr Leu Ser Leu Thr Cys Ser Phe Ser Gly Leu Ser Leu Ser Thr Pro
                20                  25                  30

Gly Ile Gly Val Gly Trp Ile Arg Gln Pro Ala Gly Lys Gly Leu Glu
            35                  40                  45

Trp Leu Ala His Ile Trp Trp Asn Asp Ala Lys Ser Tyr Asn Thr Ala
        50                  55                  60

Leu Lys Ser Arg Leu Thr Ile Ser Lys Asp Thr Ser Asn Asn Gln Val
 65                  70                  75                  80

Phe Leu Lys Ile Ala Ser Val Asp Thr Thr His Thr Ala Thr Tyr Tyr
                    85                  90                  95

Cys Val Val Ile Gly Tyr Tyr Gly Ser Thr Ala Gly Phe Ala Tyr Trp
                100                 105                 110

Gly Gln Gly Thr Leu Val Thr Val Ser Ala
            115                 120

<210> SEQ ID NO 55
```

```
<211> LENGTH: 106
<212> TYPE: PRT
<213> ORGANISM: Artificial Sequence
<220> FEATURE:
<223> OTHER INFORMATION: Synthetic Construct

<400> SEQUENCE: 55

Asp Ile Gln Met Asn Gln Ser Pro Ala Leu Met Ser Ala Ser Pro Gly
1               5                   10                  15

Glu Lys Val Thr Met Thr Cys Ser Ala Ser Ser Val Ser Ser Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Ile Lys
            100                 105

<210> SEQ ID NO 56
<211> LENGTH: 122
<212> TYPE: PRT
<213> ORGANISM: Artificial Sequence
<220> FEATURE:
<223> OTHER INFORMATION: Synthetic Construct

<400> SEQUENCE: 56

Glu Val Lys Leu Val Glu Ser Gly Pro Gly Ile Leu Gln Pro Ser Gln
1               5                   10                  15

Thr Leu Ser Leu Thr Cys Ser Phe Ser Gly Phe Ser Leu Asn Ser Tyr
            20                  25                  30

Gly Phe Gly Ile Gly Trp Ile Arg Gln Pro Ser Gly Lys Gly Leu Glu
        35                  40                  45

Trp Leu Thr His Ile Trp Trp Asn Gly Asn Lys Tyr Tyr Asn Thr Thr
    50                  55                  60

Leu Lys Ser Arg Leu Thr Ile Ser Lys Asp Thr Ser Asn Asn Gln Val
65                  70                  75                  80

Phe Leu Lys Ile Ala Ser Leu Asp Thr Ala Asp Thr Ala Thr Tyr Tyr
                85                  90                  95

Cys Ala Leu Ile His Tyr Tyr Gly Asn Ser Tyr Gly Phe Ala Tyr Trp
            100                 105                 110

Gly Gln Gly Thr Leu Val Thr Val Ser Ala
        115                 120

<210> SEQ ID NO 57
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (32)..(32)
<223> OTHER INFORMATION: Xaa at position 32 is Ser, Arg or Pro
<220> FEATURE:
<221> NAME/KEY: MISC_FEATURE
<222> LOCATION: (61)..(61)
<223> OTHER INFORMATION: Xaa at position 61 is Ser or Pro
<220> FEATURE:
<221> NAME/KEY: MISC_FEATURE
```

```
<222> LOCATION: (94)..(94)
<223> OTHER INFORMATION: Xaa at position 94 is Val, His, Ile or Phe
<220> FEATURE:
<221> NAME/KEY: MISC_FEATURE
<222> LOCATION: (102)..(102)
<223> OTHER INFORMATION: Xaa at position 102 is Thr or Val

<400> SEQUENCE: 57

Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Xaa
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Xaa Gly Val Pro
    50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys Xaa Gln Gly
                85                  90                  95

Ser His Phe Pro Trp Xaa Phe Gly Gly Gly Thr Lys Leu Glu Leu Lys
            100                 105                 110

<210> SEQ ID NO 58
<211> LENGTH: 114
<212> TYPE: PRT
<213> ORGANISM: Artificial Sequence
<220> FEATURE:
<223> OTHER INFORMATION: Synthetic Construct

<400> SEQUENCE: 58

Glu Val Lys Leu Val Glu Ser Gly Gly Gly Leu Val Lys Pro Gly Gly
1               5                   10                  15

Ser Leu Lys Ile Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ile Ser Gly Gly Thr Tyr Thr Tyr Tyr Pro Asp Ser Val
    50                  55                  60

Lys Gly Arg Phe Thr Ile Ser Arg Asp Asn Ala Arg Asn Thr Leu Asn
65                  70                  75                  80

Leu Gln Met Ser Ser Leu Arg Ala Glu Asp Thr Ala Leu Tyr Tyr Cys
                85                  90                  95

Ala Asp Asp Gly Tyr Ile His Trp Gly Gln Gly Thr Leu Val Thr Val
            100                 105                 110

Ser Ala

<210> SEQ ID NO 59
<211> LENGTH: 112
<212> TYPE: PRT
<213> ORGANISM: Artificial Sequence
<220> FEATURE:
<223> OTHER INFORMATION: Synthetic Construct

<400> SEQUENCE: 59

Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Thr Trp Leu Leu Gln Arg Pro Gly Gln Ser
```

```
                35                  40                  45
Pro Lys Arg Leu Ile Tyr Leu Val Ser Lys Leu Asp Ser Gly Val Pro
 50                  55                  60
Asp Arg Phe Thr Gly Ser Gly Ser Gly Ala Asp Phe Thr Leu Lys Ile
 65                  70                  75                  80
Ser Arg Val Glu Ala Glu Asp Leu Gly Ile Tyr Tyr Cys Val Gln Gly
                 85                  90                  95
Ser His Phe Pro Trp Thr Phe Gly Gly Gly Thr Lys Leu Glu Leu Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: Synthetic Construct

<400> SEQUENCE: 60

Asp Ile Val Met Thr Gln Ile Pro Leu Thr Leu Ser Val Thr Ile Gly
 1               5                  10                  15
Gln Pro Ala Ser Ile Ser Cys Lys Ser Ser Gln Ser Leu Leu Tyr Ser
             20                  25                  30
Asn Gly Lys Thr Tyr Leu Thr Trp Leu Leu Gln Arg Pro Gly Gln Ser
         35                  40                  45
Pro Lys Arg Leu Ile Tyr Leu Val Ser Lys Leu Asp Ser Gly Val Pro
 50                  55                  60
Asp Arg Phe Thr Gly Ser Gly Ser Gly Ala Asp Phe Thr Leu Lys Ile
 65                  70                  75                  80
Ser Arg Val Glu Ala Glu Asp Leu Gly Ile Tyr Tyr Cys His Gln Gly
                 85                  90                  95
Ser His Phe Pro Trp Thr Phe Gly Gly Gly Thr Lys Leu Glu Leu Lys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: Synthetic Construct

<400> SEQUENCE: 61

Asp Ile Val Met Thr Gln Ile Pro Leu Thr Leu Ser Val Thr Ile Gly
 1               5                  10                  15
Gln Pro Ala Ser Ile Ser Cys Lys Ser Ser Gln Ser Leu Leu Tyr Arg
             20                  25                  30
Asn Gly Lys Thr Tyr Leu Thr Trp Leu Leu Gln Arg Pro Gly Gln Ser
         35                  40                  45
Pro Lys Arg Leu Ile Tyr Leu Val Ser Lys Leu Asp Pro Gly Val Pro
 50                  55                  60
Asp Arg Phe Thr Gly Ser Gly Ser Gly Ala Asp Phe Thr Leu Lys Ile
 65                  70                  75                  80
Ser Arg Val Glu Ala Glu Asp Leu Gly Ile Tyr Tyr Cys His Gln Gly
                 85                  90                  95
Ser His Phe Pro Trp Thr Phe Gly Gly Gly Thr Lys Leu Glu Leu Lys
            100                 105                 110

<210> SEQ ID NO 62
<211> LENGTH: 112
<212> TYPE: PRT
```

```
<213> ORGANISM: Artificial Sequence
<220> FEATURE:
<223> OTHER INFORMATION: Synthetic Construct

<400> SEQUENCE: 62

Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Pro
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Pro Gly Val Pro
    50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys Ile Gln Gly
                85                  90                  95

Ser His Phe Pro Trp Thr Phe Gly Gly Gly Thr Lys Leu Glu Leu Lys
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: Synthetic Construct

<400> SEQUENCE: 63

Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Pro
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Pro Gly Val Pro
    50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Phe Pro Trp Val Phe Gly Gly Gly Thr Lys Leu Glu Leu Lys
            100                 105                 110

<210> SEQ ID NO 64
<211> LENGTH: 213
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Asp or Gln
<220> FEATURE:
<221> NAME/KEY: MISC_FEATURE
<222> LOCATION: (3)..(3)
<223> OTHER INFORMATION: Xaa at position 3 is Leu or Gln
<220> FEATURE:
<221> NAME/KEY: MISC_FEATURE
<222> LOCATION: (4)..(4)
<223> OTHER INFORMATION: Xaa at position 4 is Leu or Met
<220> FEATURE:
<221> NAME/KEY: MISC_FEATURE
<222> LOCATION: (5)..(5)
```

```
<223> OTHER INFORMATION: Xaa at position 5 is Thr or Asn
<220> FEATURE:
<221> NAME/KEY: MISC_FEATURE
<222> LOCATION: (27)..(27)
<223> OTHER INFORMATION: Xaa at position 27 is Ser or Pro
<220> FEATURE:
<221> NAME/KEY: MISC_FEATURE
<222> LOCATION: (29)..(29)
<223> OTHER INFORMATION: Xaa at position 29 is Val or Ala
<220> FEATURE:
<221> NAME/KEY: MISC_FEATURE
<222> LOCATION: (31)..(31)
<223> OTHER INFORMATION: Xaa at position 31 is Tyr or Ser
<220> FEATURE:
<221> NAME/KEY: MISC_FEATURE
<222> LOCATION: (52)..(52)
<223> OTHER INFORMATION: Xaa at position 52 is Asn or His
<220> FEATURE:
<221> NAME/KEY: MISC_FEATURE
<222> LOCATION: (59)..(59)
<223> OTHER INFORMATION: Xaa at position 59 is Ala or Pro
<220> FEATURE:
<221> NAME/KEY: MISC_FEATURE
<222> LOCATION: (76)..(76)
<223> OTHER INFORMATION: Xaa at position 76 is Ser or Asn
<220> FEATURE:
<221> NAME/KEY: MISC_FEATURE
<222> LOCATION: (93)..(93)
<223> OTHER INFORMATION: Xaa at position 93 is Asn, Tyr or Gly

<400> SEQUENCE: 64

Xaa Ile Xaa Xaa Xaa Gln Ser Pro Ala Leu Met Ser Ala Ser Pro Gly
 1               5                  10                  15

Glu Lys Val Thr Met Thr Cys Ser Ala Ser Xaa Ser Xaa Ser Xaa Met
            20                  25                  30

Tyr Trp Tyr Gln Gln Lys Pro Arg Ser Ser Pro Lys Pro Trp Ile Tyr
        35                  40                  45

Leu Thr Ser Xaa Leu Ala Ser Gly Val Pro Xaa Arg Phe Ser Gly Ser
    50                  55                  60

Gly Ser Gly Thr Ser Tyr Ser Leu Thr Ile Ser Xaa Met Glu Ala Glu
65                  70                  75                  80

Asp Ala Ala Thr Tyr Tyr Cys Gln Gln Trp Ser Ser Xaa Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 65
<211> LENGTH: 445
<212> TYPE: PRT
<213> ORGANISM: Artificial Sequence
<220> FEATURE:
```

-continued

```
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Glu or Gln
<220> FEATURE:
<221> NAME/KEY: MISC_FEATURE
<222> LOCATION: (3)..(3)
<223> OTHER INFORMATION: Xaa at position 3 is Lys or Gln
<220> FEATURE:
<221> NAME/KEY: MISC_FEATURE
<222> LOCATION: (5)..(5)
<223> OTHER INFORMATION: Xaa at position 5 is Lys or Val
<220> FEATURE:
<221> NAME/KEY: MISC_FEATURE
<222> LOCATION: (6)..(6)
<223> OTHER INFORMATION: Xaa at position 6 is Gln or Glu
<220> FEATURE:
<221> NAME/KEY: MISC_FEATURE
<222> LOCATION: (27)..(27)
<223> OTHER INFORMATION: Xaa at position 27 is Phe, Tyr or Leu
<220> FEATURE:
<221> NAME/KEY: MISC_FEATURE
<222> LOCATION: (30)..(30)
<223> OTHER INFORMATION: Xaa at position 30 is Ser or Asn
<220> FEATURE:
<221> NAME/KEY: MISC_FEATURE
<222> LOCATION: (31)..(31)
<223> OTHER INFORMATION: Xaa at position 31 is Thr or Ser
<220> FEATURE:
<221> NAME/KEY: MISC_FEATURE
<222> LOCATION: (32)..(32)
<223> OTHER INFORMATION: Xaa at position 32 is Tyr or Pro
<220> FEATURE:
<221> NAME/KEY: MISC_FEATURE
<222> LOCATION: (34)..(34)
<223> OTHER INFORMATION: Xaa at position 34 is Ile or Phe
<220> FEATURE:
<221> NAME/KEY: MISC_FEATURE
<222> LOCATION: (36)..(36)
<223> OTHER INFORMATION: Xaa at position 36 is Val or Ile
<220> FEATURE:
<221> NAME/KEY: MISC_FEATURE
<222> LOCATION: (43)..(43)
<223> OTHER INFORMATION: Xaa at position 43 is Ala or Ser
<220> FEATURE:
<221> NAME/KEY: MISC_FEATURE
<222> LOCATION: (51)..(51)
<223> OTHER INFORMATION: Xaa at position 51 is Ala or Thr
<220> FEATURE:
<221> NAME/KEY: MISC_FEATURE
<222> LOCATION: (57)..(57)
<223> OTHER INFORMATION: Xaa at position 57 is Asp or Gly
<220> FEATURE:
<221> NAME/KEY: MISC_FEATURE
<222> LOCATION: (58)..(58)
<223> OTHER INFORMATION: Xaa at position 58 is Asn or Ala
<220> FEATURE:
<221> NAME/KEY: MISC_FEATURE
<222> LOCATION: (60)..(60)
<223> OTHER INFORMATION: Xaa at position 60 is Ser or Tyr
<220> FEATURE:
<221> NAME/KEY: MISC_FEATURE
<222> LOCATION: (64)..(64)
<223> OTHER INFORMATION: Xaa at position 64 is Ala or Thr
<220> FEATURE:
<221> NAME/KEY: MISC_FEATURE
<222> LOCATION: (87)..(87)
<223> OTHER INFORMATION: Xaa at position 87 is Val or Leu
<220> FEATURE:
<221> NAME/KEY: MISC_FEATURE
<222> LOCATION: (89)..(89)
<223> OTHER INFORMATION: Xaa at position 89 is Thr or Ala
<220> FEATURE:
<221> NAME/KEY: MISC_FEATURE
<222> LOCATION: (90)..(90)
<223> OTHER INFORMATION: Xaa at position 90 is His or Asp
<220> FEATURE:
<221> NAME/KEY: MISC_FEATURE
<222> LOCATION: (97)..(97)
```

```
<223> OTHER INFORMATION: Xaa at position 97 is Val or Ala
<220> FEATURE:
<221> NAME/KEY: MISC_FEATURE
<222> LOCATION: (98)..(98)
<223> OTHER INFORMATION: Xaa at position 98 is Leu or Val
<220> FEATURE:
<221> NAME/KEY: MISC_FEATURE
<222> LOCATION: (100)..(100)
<223> OTHER INFORMATION: Xaa at position 100 is Gly or His
<220> FEATURE:
<221> NAME/KEY: MISC_FEATURE
<222> LOCATION: (104)..(104)
<223> OTHER INFORMATION: Xaa at position 104 is Ser or Asn
<220> FEATURE:
<221> NAME/KEY: MISC_FEATURE
<222> LOCATION: (105)..(105)
<223> OTHER INFORMATION: Xaa at position 105 is Thr or Ser
<220> FEATURE:
<221> NAME/KEY: MISC_FEATURE
<222> LOCATION: (106)..(106)
<223> OTHER INFORMATION: Xaa at position 106 is Ser, Ala or Tyr

<400> SEQUENCE: 65

Xaa Val Xaa Leu Xaa Xaa Ser Gly Pro Gly Ile Leu Gln Pro Ser Gln
  1               5                  10                  15

Thr Leu Ser Leu Thr Cys Ser Phe Ser Gly Xaa Ser Leu Xaa Xaa Xaa
             20                  25                  30

Gly Xaa Gly Xaa Gly Trp Ile Arg Gln Pro Xaa Gly Lys Gly Leu Glu
         35                  40                  45

Trp Leu Xaa His Ile Trp Trp Asn Xaa Xaa Lys Xaa Tyr Asn Thr Xaa
 50                  55                  60

Leu Lys Ser Arg Leu Thr Ile Ser Lys Asp Thr Ser Asn Asn Gln Val
 65                  70                  75                  80

Phe Leu Lys Ile Ala Ser Xaa Asp Xaa Xaa Thr Ala Thr Tyr Tyr Cys
                 85                  90                  95

Xaa Xaa Ile Xaa Tyr Tyr Gly Xaa Xaa Xaa Gly Phe Ala Tyr Trp Gly
            100                 105                 110

Gln Gly Thr Leu Val Thr Val Ser Ala Ala Lys Thr Thr Pro Pro Ser
            115                 120                 125

Val Tyr Pro Leu Ala Pro Gly Ser Ala Ala Gln Thr Asn Ser Met Val
            130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
            210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
            290                 295                 300
```

```
Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
                355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 66
<211> LENGTH: 213
<212> TYPE: PRT
<213> ORGANISM: Artificial Sequence
<220> FEATURE:
<223> OTHER INFORMATION: Synthetic Construct

<400> SEQUENCE: 66

Gln Ile Leu Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

-continued

```
<210> SEQ ID NO 67
<211> LENGTH: 446
<212> TYPE: PRT
<213> ORGANISM: Artificial Sequence
<220> FEATURE:
<223> OTHER INFORMATION: Synthetic Construct

<400> SEQUENCE: 67
```

Gln Val Gln Leu Lys Gln Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Val Gly Trp Ile Arg Gln Pro Ala Gly Lys Gly Leu Glu
        35                  40                  45

Trp Leu Ala His Ile Trp Trp Asn Asp Asn Lys Ser Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Thr His Thr Ala Thr Tyr Tyr
                85                  90                  95

Cys Val Val Ile Gly Tyr Tyr Gly Ser Thr Ser Gly Phe Ala Tyr Trp
            100                 105                 110

Gly Gln Gly Thr Leu Val Thr Val Ser Ala Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly

```
                    370                 375                 380
Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 68
<211> LENGTH: 213
<212> TYPE: PRT
<213> ORGANISM: Artificial Sequence
<220> FEATURE:
<223> OTHER INFORMATION: Synthetic Construct

<400> SEQUENCE: 68

Gln Ile Leu Leu Thr Gln Ser Pro Ala Leu Met Ser Ala Ser Pro Gly
1               5                   10                  15

Glu Lys Val Thr Met Thr Cys Ser Ala Ser Ser Ala Ser Tyr Met
            20                  25                  30

Tyr Trp Tyr Gln Gln Lys Pro Arg Ser Ser Pro Lys Pro Trp Ile Tyr
        35                  40                  45

Leu Thr Ser His Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Gly Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 69
<211> LENGTH: 446
<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Lys Gln Ser Gly Pro Gly Ile Leu Gln Pro Ser Gln
1               5                   10                  15

Thr Leu Ser Leu Thr Cys Ser Phe Ser Gly Tyr Ser Leu Ser Thr Pro
```

```
                 20                  25                  30
Gly Ile Gly Val Gly Trp Ile Arg Gln Pro Ala Gly Lys Gly Leu Glu
             35                  40                  45

Trp Leu Ala His Ile Trp Trp Asn Asp Ala Lys Ser Tyr Asn Thr Ala
 50                  55                  60

Leu Lys Ser Arg Leu Thr Ile Ser Lys Asp Thr Ser Asn Asn Gln Val
 65                  70                  75                  80

Phe Leu Lys Ile Ala Ser Val Asp Thr Thr His Thr Ala Thr Tyr Tyr
                 85                  90                  95

Cys Val Val Ile Gly Tyr Tyr Gly Ser Thr Ala Gly Phe Ala Tyr Trp
                100                 105                 110

Gly Gln Gly Thr Leu Val Thr Val Ser Ala Ala Lys Thr Thr Pro Pro
            115                 120                 125

Ser Val Tyr Pro Leu Ala Pro Gly Ser Ala Ala Gln Thr Asn Ser Met
        130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445
```

```
<210> SEQ ID NO 70
<211> LENGTH: 213
<212> TYPE: PRT
<213> ORGANISM: Artificial Sequence
<220> FEATURE:
<223> OTHER INFORMATION: Synthetic Construct

<400> SEQUENCE: 70
```

| Gln | Ile | Leu | Leu | Thr | Gln | Ser | Pro | Ala | Leu | Met | Ser | Ala | Ser | Pro | Gly |
|---|---|---|---|---|---|---|---|---|---|---|---|---|---|---|---|
| 1 |  |  |  | 5 |  |  |  |  | 10 |  |  |  |  | 15 |  |

| Glu | Lys | Val | Thr | Met | Thr | Cys | Ser | Ala | Ser | Pro | Ser | Val | Ser | Tyr | Met |
|---|---|---|---|---|---|---|---|---|---|---|---|---|---|---|---|
|  |  |  | 20 |  |  |  |  | 25 |  |  |  |  | 30 |  |  |

| Tyr | Trp | Tyr | Gln | Gln | Lys | Pro | Arg | Ser | Ser | Pro | Lys | Pro | Trp | Ile | Tyr |
|---|---|---|---|---|---|---|---|---|---|---|---|---|---|---|---|
|  |  | 35 |  |  |  |  | 40 |  |  |  |  | 45 |  |  |  |

| Leu | Thr | Ser | His | Leu | Ala | Ser | Gly | Val | Pro | Ala | Arg | Phe | Ser | Gly | Ser |
|---|---|---|---|---|---|---|---|---|---|---|---|---|---|---|---|
|  | 50 |  |  |  |  | 55 |  |  |  |  | 60 |  |  |  |  |

| Gly | Ser | Gly | Thr | Ser | Tyr | Ser | Leu | Thr | Ile | Ser | Ser | Met | Glu | Ala | Glu |
|---|---|---|---|---|---|---|---|---|---|---|---|---|---|---|---|
| 65 |  |  |  | 70 |  |  |  | 75 |  |  |  |  | 80 |  |  |

| Asp | Ala | Ala | Thr | Tyr | Tyr | Cys | Gln | Gln | Trp | Ser | Ser | Gly | Pro | Pro | Thr |
|---|---|---|---|---|---|---|---|---|---|---|---|---|---|---|---|
|  |  |  | 85 |  |  |  |  | 90 |  |  |  |  | 95 |  |  |

| Phe | Gly | Gly | Gly | Thr | Lys | Leu | Glu | Ile | Lys | Arg | Ala | Asp | Ala | Ala | Pro |
|---|---|---|---|---|---|---|---|---|---|---|---|---|---|---|---|
|  |  |  | 100 |  |  |  |  | 105 |  |  |  |  | 110 |  |  |

| Thr | Val | Ser | Ile | Phe | Pro | Pro | Ser | Ser | Glu | Gln | Leu | Thr | Ser | Gly | Gly |
|---|---|---|---|---|---|---|---|---|---|---|---|---|---|---|---|
|  |  | 115 |  |  |  |  | 120 |  |  |  |  | 125 |  |  |  |

| Ala | Ser | Val | Val | Cys | Phe | Leu | Asn | Asn | Phe | Tyr | Pro | Lys | Asp | Ile | Asn |
|---|---|---|---|---|---|---|---|---|---|---|---|---|---|---|---|
|  | 130 |  |  |  |  | 135 |  |  |  |  | 140 |  |  |  |  |

| Val | Lys | Trp | Lys | Ile | Asp | Gly | Ser | Glu | Arg | Gln | Asn | Gly | Val | Leu | Asn |
|---|---|---|---|---|---|---|---|---|---|---|---|---|---|---|---|
| 145 |  |  |  |  | 150 |  |  |  |  | 155 |  |  |  |  | 160 |

| Ser | Trp | Thr | Asp | Gln | Asp | Ser | Lys | Asp | Ser | Thr | Tyr | Ser | Met | Ser | Ser |
|---|---|---|---|---|---|---|---|---|---|---|---|---|---|---|---|
|  |  |  |  | 165 |  |  |  |  | 170 |  |  |  |  | 175 |  |

| Thr | Leu | Thr | Leu | Thr | Lys | Asp | Glu | Tyr | Glu | Arg | His | Asn | Ser | Tyr | Thr |
|---|---|---|---|---|---|---|---|---|---|---|---|---|---|---|---|
|  |  |  | 180 |  |  |  |  | 185 |  |  |  |  | 190 |  |  |

| Cys | Glu | Ala | Thr | His | Lys | Thr | Ser | Thr | Ser | Pro | Ile | Val | Lys | Ser | Phe |
|---|---|---|---|---|---|---|---|---|---|---|---|---|---|---|---|
|  |  |  | 195 |  |  |  |  | 200 |  |  |  |  | 205 |  |  |

| Asn | Arg | Asn | Glu | Cys |
|---|---|---|---|---|
|  |  |  | 210 |  |

```
<210> SEQ ID NO 71
<211> LENGTH: 213
<212> TYPE: PRT
<213> ORGANISM: Artificial Sequence
<220> FEATURE:
<223> OTHER INFORMATION: Synthetic Construct

<400> SEQUENCE: 71
```

| Gln | Ile | Leu | Leu | Thr | Gln | Ser | Pro | Ala | Leu | Met | Ser | Ala | Ser | Pro | Gly |
|---|---|---|---|---|---|---|---|---|---|---|---|---|---|---|---|
| 1 |  |  |  | 5 |  |  |  |  | 10 |  |  |  |  | 15 |  |

| Glu | Lys | Val | Thr | Met | Thr | Cys | Ser | Ala | Ser | Ser | Ala | Ser | Tyr | Met |
|---|---|---|---|---|---|---|---|---|---|---|---|---|---|---|
|  |  |  | 20 |  |  |  |  | 25 |  |  |  |  | 30 |  |

| Tyr | Trp | Tyr | Gln | Gln | Lys | Pro | Arg | Ser | Ser | Pro | Lys | Pro | Trp | Ile | Tyr |
|---|---|---|---|---|---|---|---|---|---|---|---|---|---|---|---|
|  |  | 35 |  |  |  |  | 40 |  |  |  |  | 45 |  |  |  |

| Leu | Thr | Ser | His | Leu | Ala | Ser | Gly | Val | Pro | Ala | Arg | Phe | Ser | Gly | Ser |
|---|---|---|---|---|---|---|---|---|---|---|---|---|---|---|---|
|  | 50 |  |  |  |  | 55 |  |  |  |  | 60 |  |  |  |  |

| Gly | Ser | Gly | Thr | Ser | Tyr | Ser | Leu | Thr | Ile | Ser | Ser | Met | Glu | Ala | Glu |
|---|---|---|---|---|---|---|---|---|---|---|---|---|---|---|---|
| 65 |  |  |  | 70 |  |  |  | 75 |  |  |  |  | 80 |  |  |

| Asp | Ala | Ala | Thr | Tyr | Tyr | Cys | Gln | Gln | Trp | Ser | Ser | Gly | Pro | Pro | Thr |
|---|---|---|---|---|---|---|---|---|---|---|---|---|---|---|---|
|  |  |  | 85 |  |  |  |  | 90 |  |  |  |  | 95 |  |  |

```
Phe Gly Gly Gly Thr Lys Leu Glu Ile Lys Arg Ala Asp Ala Ala Pro
                100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 72
<211> LENGTH: 446
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Lys Gln Ser Gly Pro Gly Ile Leu Gln Pro Ser Gln
1               5                   10                  15

Thr Leu Ser Leu Thr Cys Ser Phe Ser Gly Leu Ser Leu Ser Thr Pro
            20                  25                  30

Gly Ile Gly Val Gly Trp Ile Arg Gln Pro Ala Gly Lys Gly Leu Glu
        35                  40                  45

Trp Leu Ala His Ile Trp Trp Asn Asp Ala Lys Ser Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Thr His Thr Ala Thr Tyr Tyr
                85                  90                  95

Cys Val Val Ile Gly Tyr Tyr Gly Ser Thr Ala Gly Phe Ala Tyr Trp
            100                 105                 110

Gly Gln Gly Thr Leu Val Thr Val Ser Ala Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
```

```
                     245                 250                 255
Lys Val Thr Cys Val Val Asp Ile Ser Lys Asp Pro Glu Val
            260                 265                 270

Gln Phe Ser Trp Phe Val Asp Asp Val Glu Val His Thr Ala Gln Thr
                275                 280                 285

Gln Pro Arg Glu Glu Gln Phe Asn Ser Thr Phe Arg Ser Val Ser Glu
            290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
            370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
                420                 425                 430

Asn His His Thr Glu Lys Ser Leu Ser His Ser Pro Gly Lys
                435                 440                 445

<210> SEQ ID NO 73
<211> LENGTH: 213
<212> TYPE: PRT
<213> ORGANISM: Artificial Sequence
<220> FEATURE:
<223> OTHER INFORMATION: Synthetic Construct

<400> SEQUENCE: 73

Asp Ile Gln Met Asn Gln Ser Pro Ala Leu Met Ser Ala Ser Pro Gly
1               5                   10                  15

Glu Lys Val Thr Met Thr Cys Ser Ala Ser Ser Val Ser Ser Met
            20                  25                  30

Tyr Trp Tyr Gln Gln Lys Pro Arg Ser Ser Pro Lys Pro Trp Ile Tyr
                35                  40                  45

Leu Thr Ser Asn Leu Ala Ser Gly Val Pro Pro Arg Phe Ser Gly Ser
        50                  55                  60

Gly Ser Gly Thr Ser Tyr Ser Leu Thr Ile Ser Asn Met Glu Ala Glu
65              70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175
```

```
Thr Leu Thr Leu Thr Lys Asp Glu Tyr Glu Arg His Asn Ser Tyr Thr
            180                 185                 190
Cys Glu Ala Thr His Lys Thr Ser Thr Ser Pro Ile Val Lys Ser Phe
            195                 200                 205
Asn Arg Asn Glu Cys
            210

<210> SEQ ID NO 74
<211> LENGTH: 446
<212> TYPE: PRT
<213> ORGANISM: Artificial Sequence
<220> FEATURE:
<223> OTHER INFORMATION: Synthetic Construct

<400> SEQUENCE: 74

Glu Val Lys Leu Val Glu Ser Gly Pro Gly Ile Leu Gln Pro Ser Gln
1               5                   10                  15
Thr Leu Ser Leu Thr Cys Ser Phe Ser Gly Phe Ser Leu Asn Ser Tyr
            20                  25                  30
Gly Phe Gly Ile Gly Trp Ile Arg Gln Pro Ser Gly Lys Gly Leu Glu
        35                  40                  45
Trp Leu Thr His Ile Trp Trp Asn Gly Asn Lys Tyr Tyr Asn Thr Thr
50                  55                  60
Leu Lys Ser Arg Leu Thr Ile Ser Lys Asp Thr Ser Asn Asn Gln Val
65                  70                  75                  80
Phe Leu Lys Ile Ala Ser Leu Asp Thr Ala Asp Thr Ala Thr Tyr Tyr
                85                  90                  95
Cys Ala Leu Ile His Tyr Tyr Gly Asn Ser Tyr Gly Phe Ala Tyr Trp
            100                 105                 110
Gly Gln Gly Thr Leu Val Thr Val Ser Ala Ala Lys Thr Thr Pro Pro
        115                 120                 125
Ser Val Tyr Pro Leu Ala Pro Gly Ser Ala Ala Gln Thr Asn Ser Met
    130                 135                 140
Val Thr Leu Gly Cys Leu Val Lys Gly Tyr Phe Pro Glu Pro Val Thr
145                 150                 155                 160
Val Thr Trp Asn Ser Gly Ser Leu Ser Ser Gly Val His Thr Phe Pro
                165                 170                 175
Ala Val Leu Gln Ser Asp Leu Tyr Thr Leu Ser Ser Ser Val Thr Val
            180                 185                 190
Pro Ser Ser Thr Trp Pro Ser Glu Thr Val Thr Cys Asn Val Ala His
        195                 200                 205
Pro Ala Ser Ser Thr Lys Val Asp Lys Lys Ile Val Pro Arg Asp Cys
    210                 215                 220
Gly Cys Lys Pro Cys Ile Cys Thr Val Pro Glu Val Ser Ser Val Phe
225                 230                 235                 240
Ile Phe Pro Pro Lys Pro Lys Asp Val Leu Thr Ile Thr Leu Thr Pro
                245                 250                 255
Lys Val Thr Cys Val Val Val Asp Ile Ser Lys Asp Asp Pro Glu Val
            260                 265                 270
Gln Phe Ser Trp Phe Val Asp Asp Val Glu Val His Thr Ala Gln Thr
        275                 280                 285
Gln Pro Arg Glu Glu Gln Phe Asn Ser Thr Phe Arg Ser Val Ser Glu
    290                 295                 300
Leu Pro Ile Met His Gln Asp Trp Leu Asn Gly Lys Glu Phe Lys Cys
305                 310                 315                 320
```

```
Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 75
<211> LENGTH: 219
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (32)..(32)
<223> OTHER INFORMATION: Xaa at position 32 is Ser, Arg or Pro
<220> FEATURE:
<221> NAME/KEY: MISC_FEATURE
<222> LOCATION: (61)..(61)
<223> OTHER INFORMATION: Xaa at position 61 is Ser or Pro
<220> FEATURE:
<221> NAME/KEY: MISC_FEATURE
<222> LOCATION: (94)..(94)
<223> OTHER INFORMATION: Xaa at position 94 is Val, His, Ile or Phe
<220> FEATURE:
<221> NAME/KEY: MISC_FEATURE
<222> LOCATION: (102)..(102)
<223> OTHER INFORMATION: Xaa at position 102 is Thr or Val

<400> SEQUENCE: 75

Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Xaa
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Xaa Gly Val Pro
50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys Xaa Gln Gly
                85                  90                  95

Ser His Phe Pro Trp Xaa Phe Gly Gly Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160
```

Gln Asn Gly Val Leu Asn Ser Trp Thr Asp Gln Ser Lys Asp Ser
            165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
            210                 215

<210> SEQ ID NO 76
<211> LENGTH: 438
<212> TYPE: PRT
<213> ORGANISM: Artificial Sequence
<220> FEATURE:
<223> OTHER INFORMATION: Synthetic Construct

<400> SEQUENCE: 76

Glu Val Lys Leu Val Glu Ser Gly Gly Gly Leu Val Lys Pro Gly Gly
1               5                   10                  15

Ser Leu Lys Ile Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ile Ser Gly Gly Thr Tyr Thr Tyr Tyr Pro Asp Ser Val
    50                  55                  60

Lys Gly Arg Phe Thr Ile Ser Arg Asp Asn Ala Arg Asn Thr Leu Asn
65                  70                  75                  80

Leu Gln Met Ser Ser Leu Arg Ala Glu Asp Thr Ala Leu Tyr Tyr Cys
                85                  90                  95

Ala Asp Asp Gly Tyr Ile His Trp Gly Gln Gly Thr Leu Val Thr Val
            100                 105                 110

Ser Ala Ala Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
    130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Val Pro Arg Asp Cys Gly Cys Lys Pro Cys Ile Cys Thr
    210                 215                 220

Val Pro Glu Val Ser Ser Val Phe Ile Phe Pro Pro Lys Pro Lys Asp
225                 230                 235                 240

Val Leu Thr Ile Thr Leu Thr Pro Lys Val Thr Cys Val Val Val Asp
                245                 250                 255

Ile Ser Lys Asp Asp Pro Glu Val Gln Phe Ser Trp Phe Val Asp Asp
            260                 265                 270

Val Glu Val His Thr Ala Gln Thr Gln Pro Arg Glu Glu Gln Phe Asn
        275                 280                 285

Ser Thr Phe Arg Ser Val Ser Glu Leu Pro Ile Met His Gln Asp Trp
    290                 295                 300

Leu Asn Gly Lys Glu Phe Lys Cys Arg Val Asn Ser Ala Ala Phe Pro

```
                305                 310                 315                 320
Ala Pro Ile Glu Lys Thr Ile Ser Lys Thr Lys Gly Arg Pro Lys Ala
                325                 330                 335

Pro Gln Val Tyr Thr Ile Pro Pro Lys Glu Gln Met Ala Lys Asp
            340                 345                 350

Lys Val Ser Leu Thr Cys Met Ile Thr Asp Phe Phe Pro Glu Asp Ile
            355                 360                 365

Thr Val Glu Trp Gln Trp Asn Gly Gln Pro Ala Glu Asn Tyr Lys Asn
            370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His His Thr Glu Lys Ser Leu
                420                 425                 430

Ser His Ser Pro Gly Lys
            435

<210> SEQ ID NO 77
<211> LENGTH: 219
<212> TYPE: PRT
<213> ORGANISM: Artificial Sequence
<220> FEATURE:
<223> OTHER INFORMATION: Synthetic Construct

<400> SEQUENCE: 77

Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys Val Gln Gly
                85                  90                  95

Ser His Phe Pro Trp Thr Phe Gly Gly Gly Thr Lys Leu Glu Leu Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 78
```

<211> LENGTH: 219
<212> TYPE: PRT
<213> ORGANISM: Artificial Sequence
<220> FEATURE:
<223> OTHER INFORMATION: Synthetic Construct

<400> SEQUENCE: 78

Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys His Gln Gly
                85                  90                  95

Ser His Phe Pro Trp Thr Phe Gly Gly Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 79
<211> LENGTH: 219
<212> TYPE: PRT
<213> ORGANISM: Artificial Sequence
<220> FEATURE:
<223> OTHER INFORMATION: Synthetic Construct

<400> SEQUENCE: 79

Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Arg
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Pro Gly Val Pro
    50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys His Gln Gly
                85                  90                  95

Ser His Phe Pro Trp Thr Phe Gly Gly Gly Thr Lys Leu Glu Leu Lys
            100                 105                 110

```
Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
                195                 200                 205

Pro Ile Val Lys Ser Phe Asn Arg Asn Glu Cys
        210                 215
```

<210> SEQ ID NO 80
<211> LENGTH: 219
<212> TYPE: PRT
<213> ORGANISM: Artificial Sequence
<220> FEATURE:
<223> OTHER INFORMATION: Synthetic Construct

<400> SEQUENCE: 80

```
Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Pro
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Pro Gly Val Pro
    50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys Ile Gln Gly
                85                  90                  95

Ser His Phe Pro Trp Thr Phe Gly Gly Gly Thr Lys Leu Glu Leu Lys
                100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
                195                 200                 205

Pro Ile Val Lys Ser Phe Asn Arg Asn Glu Cys
        210                 215
```

<210> SEQ ID NO 81
<211> LENGTH: 219
<212> TYPE: PRT
<213> ORGANISM: Artificial Sequence
<220> FEATURE:

<223> OTHER INFORMATION: Synthetic Construct

<400> SEQUENCE: 81

```
Asp Ile Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Tyr Pro
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Pro Gly Val Pro
    50                  55                  60

Asp Arg Phe Thr Gly Ser Gly Ser Gly Ala Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Phe Pro Trp Val Phe Gly Gly Gly Thr Lys Leu Glu Leu Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Ser Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 82
<211> LENGTH: 215
<212> TYPE: PRT
<213> ORGANISM: Artificial Sequence
<220> FEATURE:
<223> OTHER INFORMATION: Synthetic Construct

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125
```

```
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 83
<211> LENGTH: 443
<212> TYPE: PRT
<213> ORGANISM: Artificial Sequence
<220> FEATURE:
<223> OTHER INFORMATION: Synthetic Construct

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
                20                  25                  30

Pro Ile Ser Trp Val Arg Gln Ala Pro Gly Gln Gly Leu Glu Trp Met
                35                  40                  45

Gly Asn Phe His Pro Tyr Leu Gly Val Thr Asn Tyr Val Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
```

```
                275                 280                 285
Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly
            435                 440

<210> SEQ ID NO 84
<211> LENGTH: 215
<212> TYPE: PRT
<213> ORGANISM: Artificial Sequence
<220> FEATURE:
<223> OTHER INFORMATION: Synthetic Construct

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
                20                  25                  30

Tyr Leu Phe Trp Tyr Gln Gln Lys Pro Gly Lys Ala Pro Lys Leu Leu
            35                  40                  45

Ile Tyr Arg Thr Ser Thr Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205
```

-continued

```
Ser Phe Asn Arg Gly Glu Cys
    210                 215

<210> SEQ ID NO 85
<211> LENGTH: 443
<212> TYPE: PRT
<213> ORGANISM: Artificial Sequence
<220> FEATURE:
<223> OTHER INFORMATION: Synthetic Construct

<400> SEQUENCE: 85

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Asn Tyr Leu Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

```
Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly
            435                 440

<210> SEQ ID NO 86
<211> LENGTH: 7
<212> TYPE: PRT
<213> ORGANISM: Artificial Sequence
<220> FEATURE:
<223> OTHER INFORMATION: Synthetic Construct

<400> SEQUENCE: 86

Asp Thr Asn Phe Pro Ile Cys
1               5

<210> SEQ ID NO 87
<211> LENGTH: 26
<212> TYPE: PRT
<213> ORGANISM: Artificial Sequence
<220> FEATURE:
<223> OTHER INFORMATION: Synthetic Construct

<400> SEQUENCE: 87

Asp Thr His Phe Pro Ile Cys Gly Pro Gly Pro Gly Ile Ser Gln Ala
1               5                   10                  15

Val His Ala Ala His Ala Glu Ile Asn Glu
            20                  25

<210> SEQ ID NO 88
<211> LENGTH: 20
<212> TYPE: PRT
<213> ORGANISM: Homo sapiens

<400> SEQUENCE: 88

Ile Cys Ile Phe Cys Cys Gly Cys Cys His Arg Ser Lys Cys Gly Met
1               5                   10                  15

Cys Cys Lys Thr
            20

<210> SEQ ID NO 89
<211> LENGTH: 22
<212> TYPE: PRT
<213> ORGANISM: Homo sapiens

<400> SEQUENCE: 89

Phe Pro Ile Cys Ile Phe Cys Cys Gly Cys Cys His Arg Ser Lys Cys
1               5                   10                  15

Gly Met Cys Cys Lys Thr
            20

<210> SEQ ID NO 90
<211> LENGTH: 61
<212> TYPE: PRT
<213> ORGANISM: Homo sapiens
```

```
<400> SEQUENCE: 90

Gly Ser Val Phe Pro Gln Gln Thr Gly Gln Leu Ala Glu Leu Gln Pro
1               5                   10                  15

Gln Asp Arg Ala Gly Ala Arg Ala Ser Trp Met Pro Met Phe Gln Arg
            20                  25                  30

Arg Arg Arg Arg Asp Thr His Phe Pro Ile Cys Ile Phe Cys Cys Gly
        35                  40                  45

Cys Cys His Arg Ser Lys Cys Gly Met Cys Cys Lys Thr
    50                  55                  60
```

ANTI-HEPCIDIN-25 SELECTIVE ANTIBODIES AND USES THEREOF

This is the national phase application, under 35 USC 371, for PCT/US2009/052044, filed Jul. 29, 2009, which claims the benefit, under 35 USC 119(e), of U.S. provisional application 61/086,557 filed Aug. 6, 2008.

The present invention is in the field of medicine, particularly in the field of antibodies against human hepcidin-25. More specifically, the present invention concerns treatment of certain diseases, such as anemia, by administering anti-hepcidin-25 selective antibodies to patients in need thereof. The present invention further concerns methods and kits for detecting hepcidin-25 and/or diagnosing a disease condition characterized by elevated levels of hepcidin-25.

Human hepcidin, a polypeptide expressed predominantly by hepatocytes, is believed to be an important iron-regulatory protein that negatively regulates intestinal iron absorption, iron recycling by macrophages, and iron mobilization from hepatic iron stores. Overproduction of hepcidin appears to play a primary role in the pathophysiology of anemia and/or in anemia of chronic disease.

Presently, suitable and effective therapies for anemia and/or for anemia of chronic disease are limited. Specifically, erythropoietin administration is effective in only about 50% of all the patients and is associated with undesirable side effects. Furthermore, transfusions are undesirable due to contamination, infection and iron overload.

Human hepcidin is encoded as an 84 amino acid prepropeptide containing a typical N-terminal 24 amino acid endoplasmic reticulum targeting signal sequence, and a 35 amino acid proregion with a consensus furin cleavage site immediately followed by the C-terminal 25 amino acid bioactive iron-regulatory hormone (hepcidin-25, SEQ ID NO:1). Various N-terminal truncated forms of hepcidin, such as hepcidin-20 (e.g., for humans, amino acids 6-25 of SEQ ID NO:1) and hepcidin-22 (e.g., for humans, amino acids 4-25 of SEQ ID NO:1) are also known to form in vivo. However, hepcidin-25 is thought to be the most, if not the only, physiologically-relevant form of hepcidin in humans. Therapies that selectively regulate the concentration of hepcidin-25, as opposed to the precursor or truncated forms, are particularly desirable. In particular, antibodies that selectively bind to hepcidin-25 as opposed to precursor and truncated forms would provide numerous advantages in the treatment or diagnosis of disorders associated with elevated levels of hepcidin-25. For example, as compared to non-selective hepcidin antibodies, high affinity hepcidin-25 selective antibodies would reduce the risk for side-effects and the clinical dose required for effective treatment would be lower because the therapeutic antibodies would not bind to physiologically-irrelevant forms of hepcidin. While non-human polyclonal and monoclonal antibodies to hepcidin have been reported previously (see, e.g., U.S. Patent Application Publications 2006/0019339, 2007/0224186, and 2008/0213277), there still remains in the art a great need for monoclonal antibodies that selectively bind to hepcidin-25. Thus, one aspect of the invention is the provision of antibodies that selectively bind human hepcidin-25 within amino acids 1 to 7, inclusive, of hepcidin-25. Such antibodies are useful for increasing serum iron levels, reticulocyte count, red blood cell count, hemoglobin, and/or hematocrit in a human for the treatment of a disease, condition, or disorder such as anemia.

Additionally, existing immunoassays for hepcidin do not differentiate the active, physiologically relevant hepcidin-25 from inactive, physiologically non-relevant hepcidin species (see, for example, Kemna, E. H., et al., Haematologica, 93(1): 90-7 (2008); Roe M. A., et al., Br J Nutr., 97:544-9 (2007); and, Luukkonen S. and Punnonen K., Clin Chem Lab Med., 44:1361-2 (2006)). Presently, the only methods currently available to selectively assay for hepcidin-25 involve LC/MS (liquid chromatography/mass spectroscopy) or similar cumbersome methods which require the separation of the various forms of hepcidin (see, for example, Gutierrez, J. A., et al., BioTechniques, 38:S13-S17 (2005), Murphy, et al., Blood, 110:1048-54 (2007), and Kemna, E. H., et al., Clin. Chem., 53:620-8 (2007)). While these assays may be accurate and precise, their complexity, expense, and the high level of operator expertise required inhibit their routine implementation. Accordingly, there is also a great need for antibodies that selectively bind with high affinity to human hepcidin-25 for their application in immunoassays for the detection or measurement of hepcidin-25. Thus, another aspect of the invention provides methods of using hepcidin-25 selective antibodies in relatively simple yet highly sensitive, robust, and selective immunoassays for the detection and measurement of hepcidin-25 in mammalian tissues and biological fluids.

The present invention provides antibodies that selectively bind human hepcidin-25 within amino acids 1 to 7, inclusive, of hepcidin-25. In one embodiment, an antibody of the invention selectively binds a polypeptide having the amino acid sequence as shown in SEQ ID NO: 1, as opposed to related precursors and truncated polypeptides, and comprises six CDRs selected from the group consisting of: (i) LCDR1, LCDR2, LCDR3, HCDR1, HCDR2, and HCDR3 having the amino acid sequences as shown in SEQ ID NOs: 9, 10, 11, 32, 33 and 34, respectively; (ii) LCDR1, LCDR2, LCDR3, HCDR1, HCDR2, and HCDR3 having the amino acid sequences as shown in SEQ ID NOs: 12, 13, 14, 35, 36, and 37, respectively; (iii) LCDR1, LCDR2, LCDR3, HCDR1, HCDR2, and HCDR3 having the amino acid sequences as shown in SEQ ID NOs: 45, 13, 14, 35, 36, and 37, respectively; (iv) LCDR1, LCDR2, LCDR3, HCDR1, HCDR2, and HCDR3 having the amino acid sequences as shown in SEQ ID NOs: 12, 13, 14, 38, 36 and 37, respectively; (v) LCDR1, LCDR2, LCDR3, HCDR1, HCDR2, and HCDR3 having the amino acid sequences as shown in SEQ ID NOs: 15, 10, 16, 39, 40 and 41, respectively; (vi) LCDR1, LCDR2, LCDR3, HCDR1, HCDR2, and HCDR3 having the amino acid sequences as shown in SEQ ID NOs: 20, 21, 22, 42, 43, and 44, respectively; (vii) LCDR1, LCDR2, LCDR3, HCDR1, HCDR2, and HCDR3 having the amino acid sequences as shown in SEQ ID NOs: 20, 21, 23, 42, 43 and 44, respectively; (viii) LCDR1, LCDR2, LCDR3, HCDR1, HCDR2, and HCDR3 having the amino acid sequences as shown in SEQ ID NOs: 24, 25, 23, 42, 43 and 44, respectively; (ix) LCDR1, LCDR2, LCDR3, HCDR1, HCDR2, and HCDR3 having the amino acid sequences as shown in SEQ ID NOs: 26, 25, 27, 42, 43 and 44, respectively; and (x) LCDR1, LCDR2, LCDR3, HCDR1, HCDR2, and HCDR3 having the amino acid sequences as shown in SEQ ID NOs: 26, 25, 28, 42, 43 and 44, respectively.

In another embodiment, an antibody of the invention binds an epitope contained within amino acids 1 to 7, inclusive, of human hepcidin-25, i.e., DTHFPIC of SEQ ID NO: 1 or DTNFPIC of rodent hepcidin-25 (SEQ ID NO: 2 or 3). Preferably the antibody of the invention comprises a light chain variable region ("LCVR") polypeptide and a heavy chain variable region ("HCVR") polypeptide wherein (i) the LCVR and the HCVR polypeptides have the amino acid sequences as shown in SEQ ID NOs: 48 and 49, respectively; (ii) the LCVR and the HCVR polypeptides have the amino acid sequences as shown in SEQ ID NOs: 50 and 51, respectively; (iii) the LCVR and the HCVR polypeptides have the amino acid sequences as shown in SEQ ID NOs: 52 and 51, respectively; (iv) the LCVR and the HCVR have the amino acid sequences as shown in SEQ ID NOs: 53 and 54, respectively; (v) the LCVR and the HCVR have the amino acid sequences as shown in SEQ ID NOs: 55 and 56, respectively; (vi) the LCVR and the HCVR have the amino acid sequences as shown in SEQ ID NOs: 59 and 58 respectively; (vii) the LCVR and the HCVR have the amino acid sequences as shown in SEQ ID NOs: 60 and 58, respectively; (viii) the LCVR and the HCVR have the amino acid sequences as shown in SEQ ID NOs: 61 and 58, respectively; (ix) the LCVR and the HCVR have the amino acid sequences as shown in SEQ ID NOs: 62 and 58, respectively; or (x) the LCVR and the HCVR have the amino acid sequences as shown in SEQ ID NOs: 63 and 58, respectively.

In other embodiment, the invention provides isolated nucleic acid molecules encoding antibodies of the invention; vectors comprising nucleic acid molecules encoding antibodies of the invention, optionally, operably-linked to control sequences recognized by a host cell transformed with the vector; host cells comprising vectors comprising nucleic acid molecules encoding antibodies of the invention; a process for producing an antibody of the invention comprising culturing host cells comprising vectors comprising nucleic acid molecules encoding antibodies of the invention so that the nucleic acid is expressed and, optionally, recovering the antibody from the host cell culture medium.

In another embodiment, the invention provides a pharmaceutical composition comprising an antibody of the invention and a pharmaceutically acceptable carrier or diluent. Preferably, the pharmaceutical composition comprises a homogeneous or substantially homogeneous population of a monoclonal antibody of the invention and a pharmaceutically acceptable carrier or diluent.

In another embodiment, the invention provides a human engineered monoclonal antibody that selectively binds mature human hepcidin for use in therapy.

In another embodiment, the invention provides a human engineered monoclonal antibody that selectively binds mature human hepcidin for use in treating or preventing anemia in a human subject.

The invention also embodies the use of a human engineered monoclonal antibody that selectively binds mature human hepcidin for the preparation of a medicament. The invention further embodies the use of a human engineered monoclonal antibody that selectively binds mature human hepcidin in a method for increasing serum iron levels, reticulocyte count, red blood cell count, hemoglobin, and/or hematocrit in an animal, preferably a mammalian species, more preferably a human subject.

The invention further provides a method of increasing serum iron levels, reticulocyte count, red blood cell count, hemoglobin, and/or hematocrit that comprises administering to a human subject in need thereof, an effective amount of a human engineered monoclonal antibody that binds mature human hepcidin.

Another embodiment of the invention provides a method for treating a disease, condition or disorder, in a human subject, which benefits from an increase in serum iron levels, reticulocyte count, red blood cell count, hemoglobin, and/or hematocrit, including, but not limited to, anemia, e.g., anemia resulting from infection, inflammation, chronic disease, and/or cancer.

The invention also provides a method for measuring the amount of hepcidin-25 in a sample of tissue or biological fluid obtained from a mammal, said method comprising the steps of; (i) obtaining a sample of tissue or biological fluid from said mammal; (ii) causing said sample to contact a hepcidin-25 selective antibody or fragment thereof; and (iii) detecting the amount of hepcidin-25 in said sample directly or indirectly by quantitative, semi-quantitative or qualitative means.

In another embodiment, the antibodies of the invention are useful in quantifying the amount of hepcidin-25 protein in a sample of tissue or biological fluid obtained from a mammal comprising; (i) coating a solid support with a first antibody that binds an epitope contained within amino acids 5 to 25, inclusive, of SEQ ID NO: 1, SEQ ID NO:3 (mouse 5-25), or SEQ ID NO: 2 (rat 5-25); (ii) obtaining a test sample of tissue or biological fluid from said mammal; (iii) applying the test sample to the antibody coated solid support; (iii) allowing any hepcidin present to form a hepcidin-first antibody complex under suitable conditions for hepcidin-first antibody binding; (iv) removing unbound sample; (v) applying a second antibody that binds an epitope contained within amino acids 1 to 7, inclusive, of human or rodent hepcidin-25, i.e., DTHFPIC or DTNFPIC respectively, to the solid support; (vi) allowing any hepcidin-25 present to form a second antibody-hepcidin-25-first antibody complex under suitable conditions for the second antibody to bind any hepcidin-25-first antibody complex and; (v) removing unbound second antibody; (vi) and detecting the presence or absence of the second antibody. The presence or absence of the second antibody can be detected either directly or indirectly and can be measured quantitatively, semi-quantitatively or qualitatively.

Figure 1:
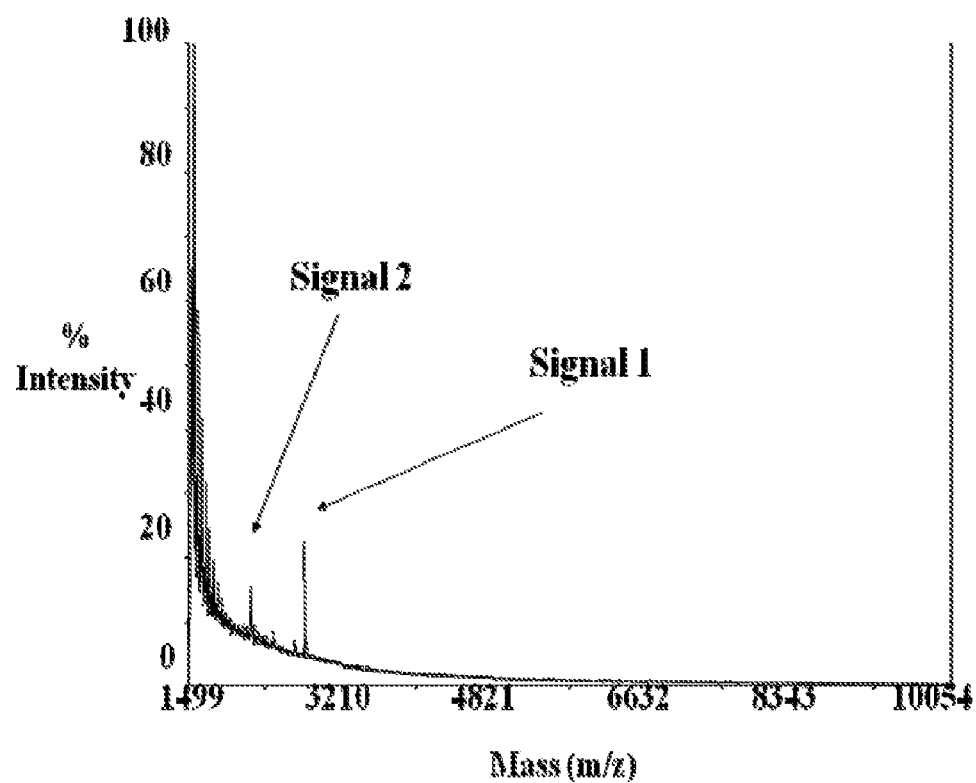
FIG. 1 depicts a MALDI-TOF mass spectrum of the forms of human hepcidin immunoprecipitated from human sera with the anti-hepcidin-25 selective Mab 3.23. Signal 1 has a mass which is consistent with the expected mass of intact human hepcidin-25 (approximate molecular weight (MW) of 2790 Daltons (Da)). Signal 2 has a mass which is consistent with the expected mass of intact human hepcidin-20 (MW of 2192 Da). As the chromatogram demonstrates, the anti-hepcidin-25 Mab 3.23 bound detectable amounts of hepcidin-25, and much lesser amounts of hepcidin-20. The Mab 3.23 did not appear to bind detectable levels of hepcidin-22 (MW 2436 Da), hepcidin-24 (MW 2674 Da), or pro-hepcidin (MW 6929 Da). The mass spectrum was generated on a MALDI-TOF mass spectrometer utilizing a positive ion, linear mode method with a-cyano-4-hydroxycinnamic acid (peptide matrix) as sample matrix essentially as described in Example 6 below.

The following abbreviations are used herein: ACN: acetonitrile, BSA: bovine serum albumin, DTT: dithiothreitol, EDTA: ethylenediamine tetraacetic acid, ELISA: enzyme linked immunosorbent assay, IMAC: immobilized metal-affinity chromatography, IPTG: isopropyl β-D-1-thiogalactopyranoside, Mab: monoclonal antibody, Mabs: monoclonal antibodies, MALDI-TOF: Matrix-Associated Laser Desorption Ionization-Time of Flight, PBS: phosphate-buffered saline, SPR: surface plasmon resonance, TFA: trifluoroacetic acid. All amino acid abbreviations used in this disclosure are those accepted by the United States Patent and Trademark Office as set forth in 37 C.F.R. §1.822 (B)(2).

The present invention provides antibodies that selectively bind hepcidin-25 by targeting an epitope contained within amino acids 1 to 7, inclusive, of hepcidin-25. Such antibodies are useful for increasing serum iron levels, reticulocyte count, red blood cell count, hemoglobin, and/or hematocrit in a human for the treatment of a disease, condition, or disorder such as anemia. Furthermore, the present invention provides methods of using such antibodies in relatively simple yet highly sensitive and selective immunoassays for the detection and/or measurement of hepcidin-25 in mammalian tissues and biological fluids.

When used herein, the term "hepcidin" refers to any form of the hepcidin protein known to be present in mammals. When used herein, the term "mature hepcidin" refers to any mature, bioactive form of the hepcidin protein expressed in mammals. When used herein, the phrase "human hepcidin" refers to any form of the hepcidin protein present in humans. When used herein, the phrase "human hepcidin-25" refers to the mature form of human hepcidin having the amino acid sequence as shown in SEQ ID NO: 1.

The general structure of an antibody is very well-known in the art. For an antibody of the IgG type, there are four amino acid chains (two "heavy" chains and two "light" chains) that are cross-linked via intra- and inter-chain disulfide bonds. When expressed in certain biological systems, antibodies having unmodified human Fc sequences are glycosylated in the Fc region. Antibodies may be glycosylated at other positions as well. The subunit structures and three-dimensional configurations of antibodies are well known in the art. Each heavy chain is comprised of an N-terminal heavy chain variable region ("HCVR") and a heavy chain constant region ("HCCR"). The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region (herein "LCVR") and a light chain constant region ("LCCR").

The variable regions of each light/heavy chain pair form the antibody binding site. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "CDRH1, CDRH2, and CDRH3" and the three CDRs of the light chain are referred to as "CDRL1, CDRL2 and CDRL3." The CDRs contain most of the residues which form specific interactions with the antigen. The assignment of amino acids to each domain is in accordance with well-known conventions (e.g., Kabat, "Sequences of Proteins of Immunological Interest," National Institutes of Health, Bethesda, Md. (1991)).

Antibodies of the present invention may have a heavy chain constant region selected from any of the immunoglobulin classes (IgA, IgD, IgG, IgM, and IgE). Preferably, antibodies of the present invention contain a constant region which is derived from human or mouse IgG Fc region.

The term "monoclonal antibody" refers to an antibody that is derived from a single copy or clone, including e.g., any eukaryotic, prokaryotic, or phage clone, and not the method by which it is produced. Preferably, a monoclonal antibody of the invention exists in a homogeneous or substantially homogeneous population.

An antibody of the present invention can be intact, i.e., comprise complete or full length constant regions, including the Fc region, or a portion or fragment of such an antibody provided that any shortened form comprises the antigen-binding portion and retains antigen-binding capability. Such shortened forms include, e.g., a Fab fragment, Fab' fragment or F(ab') 2 fragment that includes the CDRs or the variable regions of the anti-hepcidin-25 selective antibodies disclosed. Furthermore, such shortened antibody forms can be a single chain Fv fragment that may be produced by joining the DNA encoding the LCVR and HCVR with a linker sequence. (See, Pluckthun, The Pharmacology of Monoclonal Antibodies, vol. 113, Rosenburg and Moore eds., Springer-Verlag, New York, pp 269-315, 1994). Regardless of whether fragments or portions are specified, the term "antibody" as used herein includes such fragments or portions as well as single chain forms unless otherwise indicated. As long as the protein portion or protein fragment retains the ability to selectively bind hepcidin-25 and neutralize one or more bioactivities characteristic of mammalian hepcidin-25 in vivo or in vitro, it is included within the term "antibody".

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45:1628-50 (1999) and Fellouse, F. A., et al., J. Mol. Biol., 373(4):924-40 (2007)).

Tables 1 and 2 below depict preferred CDRs for the antibodies of the present invention.

TABLE 1

| Fab | LCDR1 | LCDR2 | LCDR3 |
|---|---|---|---|
| Consensus 1 | SASSSX$_1$SX$_2$MY (SEQ ID NO: 6) | LTSX$_3$LAS (SEQ ID NO: 7) | QQWSSX$_4$PPT (SEQ ID NO: 8) |
| 4C11 | SASSSVSYMY (SEQ ID NO: 9) | LTSNLAS (SEQ ID NO: 10) | QQWSSNPPT (SEQ ID NO: 11) |
| 1G8 | SASSSASYMY (SEQ ID NO: 12) | LTSHLAS (SEQ ID NO: 13) | QQWSSGPPT (SEQ ID NO: 14) |
| 1B4 | SASPSVSYMY (SEQ ID NO: 45) | LTSHLAS (SEQ ID NO: 13) | QQWSSGPPT (SEQ ID NO: 14) |

TABLE 1-continued

| Fab | LCDR1 | LCDR2 | LCDR3 |
|---|---|---|---|
| 1E3 | SASSSASYMY (SEQ ID NO: 12) | LTSHLAS (SEQ ID NO: 13) | QQWSSGPPT (SEQ ID NO: 14) |
| 3A9 | SASSSVSSMY (SEQ ID NO: 15) | LTSNLAS (SEQ ID NO: 10) | QQWSSYPPT (SEQ ID NO: 16) |
| Consensus 2 | KSSQSLLYX$_5$NGKTYLT (SEQ ID NO: 17) | LVSKLDX$_6$ (SEQ ID NO: 18) | X$_7$QGSHFPWX$_8$ (SEQ ID NO: 19) |
| 5E8 | KSSQSLLYSNGKTYLT (SEQ ID NO: 20) | LVSKLDS (SEQ ID NO: 21) | VQGSHFPWT (SEQ ID NO: 22) |
| OB3 | KSSQSLLYSNGKTYLT (SEQ ID NO: 20) | LVSKLDS (SEQ ID NO: 21) | HQGSHFPWT (SEQ ID NO: 23) |
| OB1 | KSSQSLLYRNGKTYLT (SEQ ID NO: 24) | LVSKLDP (SEQ ID NO: 25) | HQGSHFPWT (SEQ ID NO: 23) |
| OH4 | KSSQSLLYPNGKTYLT (SEQ ID NO: 26) | LVSKLDP (SEQ ID NO: 25) | IQGSHFPWT (SEQ ID NO: 27) |
| OE 1 | KSSQSLLYPNGKTYLT (SEQ ID NO: 26) | LVSKLDP (SEQ ID NO: 25) | FQGSHFPWV (SEQ ID NO: 28) |

*$X_1$ is V or A,
$X_2$ is Y or S;
$X_3$ is N or H,
$X_4$ is N, G or Y;
$X_5$ is S, R or P;
$X_6$ is S or P;
$X_7$ is V, H, I or F;
$X_8$ is T or V

TABLE 2

| Fab | HCDR1 | HCDR2 | HCDR3 |
|---|---|---|---|
| Consensus | GX$_9$SLX$_{10}$X$_{11}$X$_{12}$G X$_{13}$GX$_{14}$G (SEQ ID NO: 29) | HIWWN X$_{15}$X$_{16}$K X$_{17}$ YNTX$_{18}$LKS (SEQ ID NO: 30) | X$_{19}$YYG X$_{20}$X$_{21}$ X$_{22}$ GFAY (SEQ ID NO: 31) |
| 4C11 | GFSLSTYGIGVG (SEQ ID NO: 32) | HIWWNDNKSYNTAL KS (SEQ ID NO: 33) | IGYYGSTSGFAY (SEQ ID NO: 34) |
| 1G8 | GYSLSTPGIGVG (SEQ ID NO: 35) | HIWWNDAKSYNTAL KS (SEQ ID NO: 36) | IGYYGSTAGFAY (SEQ ID NO: 37) |
| 1B4 | GYSLSTPGIGVG (SEQ ID NO: 35) | HIWWNDAKSYNTAL KS (SEQ ID NO: 36) | IGYYGSTAGFAY (SEQ ID NO: 37) |
| 1E3 | GLSLSTPGIGVG (SEQ ID NO: 38) | HIWWNDAKSYNTAL KS (SEQ ID NO: 36) | IGYYGSTAGFAY (SEQ ID NO: 37) |
| 3A9 | GFSLNSYGFGIG (SEQ ID NO: 39) | HIWWNGNKYYNTTL KS (SEQ ID NO: 40) | IHYYGNSYGFAY (SEQ ID NO: 41) |
| Consensus 2 | GFAFSSYDMS (SEQ ID NO: 42) | TIISGGTYTYYPDS VKG (SEQ ID NO: 43) | DGYIH (SEQ ID NO: 44) |
| 5E8 | GFAFSSYDMS (SEQ ID NO: 42) | TIISGGTYTYYPDS VKG (SEQ ID NO: 43) | DGYIH (SEQ ID NO: 44) |
| OB3 | GFAFSSYDMS (SEQ ID NO: 42) | TIISGGTYTYYPDS VKG (SEQ ID NO: 43) | DGYIH (SEQ ID NO: 44) |
| OB1 | GFAFSSYDMS (SEQ ID NO: 42) | TIISGGTYTYYPDS VKG (SEQ ID NO: 43) | DGYIH (SEQ ID NO: 44) |
| OH4 | GFAFSSYDMS (SEQ ID NO: 42) | TIISGGTYTYYPDS VKG (SEQ ID NO: 43) | DGYIH (SEQ ID NO: 44) |
| OE1 | GFAFSSYDMS (SEQ ID NO: 42) | TIISGGTYTYYPDS VKG (SEQ ID NO: 43) | DGYIH (SEQ ID NO: 44) |

* $X_9$ is F, Y or L;
$X_{10}$ is S or N,
$X_{11}$ is T or S;
$X_{12}$ is Y or P,
$X_{13}$ is I or F;
$X_{14}$ is V, or I;
$X_{15}$ is D or G;
$X_{16}$ is A or N;
$X_{17}$ is S or Y;
$X_{18}$ is A or T;
$X_{19}$ is G or H;
$X_{20}$ is S or N;
$X_{21}$ is T or S;
$X_{22}$ is S, A or Y.

The present invention includes, but is not limited to, an antibody that comprises:
  a) a light chain variable region comprising;
    i) a LCDR1 having an amino acid sequence selected from the group consisting of SEQ ID NOs: 6, 9, 12, 45, 15, 17, 20, 24 and 26;
    ii) a LCDR2 having amino acid sequence selected from the group consisting of SEQ ID NOs: 7, 10, 13, 18, 21 and 25; and
    iii) a LCDR3 having an amino acid sequence selected from the group consisting of SEQ ID NOs: 8, 11, 14, 16, 19, 22, 23, 17 and 28; and
  b) a heavy chain variable region comprising:
    i) a HCDR1 having an amino acid sequence selected from the group consisting of SEQ ID NOs: 29, 32, 35, 38, 39 and 42;
    ii) a HCDR2 having an amino acid sequence selected from the group consisting of SEQ ID NOs: 30, 33, 36, 40 and 43; and
    iii) a HCDR3 having an amino acid sequence selected from the group consisting of SEQ ID NOs: 31, 24, 27, 41 and 44.

Alternatively, a preferred antibody of the invention comprises:
  a) a LCVR comprising;
    i) a LCDR1 having an amino acid sequence selected from the group consisting of SEQ ID NOs: 9, 12, 20 and 26;
    ii) a LCDR2 having an amino acid sequence selected from the group consisting of SEQ ID NOs: 10, 13, 21 and 25; and
    iii) a LCDR3 having an amino acid sequence selected from the group consisting of SEQ ID NOs: 11, 14, 23 and 27; and
  b) a HCVR comprising:
    i) a HCDR1 having an amino acid sequence selected from the group consisting of SEQ ID NOs: 32, 35 and 42;
    ii) a HCDR2 having an amino acid sequence selected from the group consisting of SEQ ID NOs: 33, 36 and 43; and
    iii) a HCDR3 having an amino acid sequence as shown in SEQ ID NO: 34, 37 and 44.

Another preferred antibody of the invention comprises a LCDR1, LCDR2, LCDR3, HCDR1, HCDR2, and HCDR3 having the amino acid sequences as shown in SEQ ID NOs: 20, 21, 22, 42, 43 and 44, respectively.

Another preferred antibody of the invention comprises a LCDR1, LCDR2, LCDR3, HCDR1, HCDR2, and HCDR3 having the amino acid sequences as shown in SEQ ID NOs: 26, 25, 28, 42, 43 and 44, respectively.

Another preferred antibody of the invention comprises a LCDR1, LCDR2, LCDR3, HCDR1, HCDR2, and HCDR3 having the amino acid sequences as shown in SEQ ID NOs: 24, 25, 23, 42, 43 and 44, respectively.

A more preferred antibody of the invention comprises a LCDR1, LCDR2, LCDR3, HCDR1, HCDR2, and HCDR3 having the amino acid sequences as shown in SEQ ID NOs: 26, 25, 27, 42, 43 and 44, respectively.

An even more preferred antibody of the invention comprises a LCDR1, LCDR2, LCDR3, HCDR1, HCDR2, and HCDR3 having the amino acid sequences as shown in SEQ ID NOs: 9, 10, 11, 32, 33, and 34, respectively.

An even more preferred antibody of the invention comprises a LCDR1, LCDR2, LCDR3, HCDR1, HCDR2, and HCDR3 having the amino acid sequences as shown in SEQ ID NOs: 12, 13, 14, 35, 36 and 37, respectively.

An even more preferred antibody of the invention comprises a LCDR1, LCDR2, LCDR3, HCDR1, HCDR2, and HCDR3 having the amino acid sequences as shown in SEQ ID NOs: 45, 13, 14, 35, 36 and 37, respectively.

A most preferred antibody of the invention comprises a LCDR1, LCDR2, LCDR3, HCDR1, HCDR2, and HCDR3 having the amino acid sequences as shown in SEQ ID NOs: 20, 21, 23, 42, 43 and 44, respectively.

A most preferred antibody of the invention comprises a LCDR1, LCDR2, LCDR3, HCDR1, HCDR2, and HCDR3 having the amino acid sequences as shown in SEQ ID NOs: 12, 13, 14, 38, 36 and 37, respectively.

A most preferred antibody of the invention comprises a LCDR1, LCDR2, LCDR3, HCDR1, HCDR2, and HCDR3 having the amino acid sequences as shown in SEQ ID NOs: 15, 10, 16, 39, 40 and 41, respectively.

A preferred antibody of the invention comprises a LCVR having an amino acid sequence selected from the group consisting of SEQ ID NOs: 46, 48, 50, 52, 53, 55, 57, 59, 60, 61, 62, and 63. Another preferred antibody of the invention comprises a HCVR having an amino acid sequence selected from the group consisting of SEQ ID NOs: 47, 49, 51, 54, 56 and 58. Another preferred antibody of the invention comprises a LCVR of SEQ ID NO: 59 and a HCVR of SEQ ID NO: 58. Another preferred antibody of the invention comprises a LCVR of SEQ ID NO: 60 and a HCVR of SEQ ID NO: 58. Another preferred antibody of the invention comprises a LCVR of SEQ ID NO: 61 and a HCVR of SEQ ID NO: 58. Another preferred antibody of the invention comprises a LCVR of SEQ ID NO: 62 and a HCVR of SEQ ID NO: 58. Another preferred antibody of the invention comprises a LCVR of SEQ ID NO: 63 and a HCVR of SEQ ID NO: 58. A most preferred antibody of the invention comprises a LCVR of SEQ ID NO: 48 and a HCVR of SEQ ID NO: 49. Another most preferred antibody of the invention comprises a LCVR of SEQ ID NO: 55 and a HCVR of SEQ ID NO: 56. Such LCVRs are preferably linked to a light chain or heavy chain constant region.

Preferred monoclonal antibodies of the invention are referred to herein as 4C11, 1G8, 1B4, 1E3, 3A9, 2, 5E8, OB3, OB1, OH4 and OE1. The SEQ ID NOs of the amino acid sequences encoding Mabs 4C11, 1G8, 1B4, 1E3, 3A9, 5E8, OB3, OB1, OH4, OE1, 3.12, 3.23 and/or various fragments thereof, are provided in Table 3 below.

TABLE 3

| Mab | LC | HC | LCVR | LCDR 1 | LCDR 2 | LCDR 3 | HCVR | HCDR 1 | HCDR 2 | HCDR 3 |
|---|---|---|---|---|---|---|---|---|---|---|
| Consensus 1 | 64 | 65 | 46 | 6 | 7 | 8 | 47 | 29 | 30 | 31 |
| 4C11 | 66 | 67 | 48 | 9 | 10 | 11 | 49 | 32 | 33 | 34 |
| 1G8 | 68 | 69 | 50 | 12 | 13 | 14 | 51 | 35 | 36 | 37 |
| 1B4 | 70 | 69 | 52 | 45 | 13 | 14 | 51 | 35 | 36 | 37 |
| 1E3 | 71 | 72 | 53 | 12 | 13 | 14 | 54 | 38 | 36 | 37 |
| 3A9 | 73 | 74 | 55 | 15 | 10 | 16 | 56 | 39 | 40 | 41 |
| Consensus 2 | 75 | 76 | 57 | 17 | 18 | 19 | 58 | 42 | 43 | 44 |
| 5E8 | 77 | 76 | 59 | 20 | 21 | 22 | 58 | 42 | 43 | 44 |
| OB3 | 78 | 76 | 60 | 20 | 21 | 23 | 58 | 42 | 43 | 44 |
| OB1 | 79 | 76 | 61 | 24 | 25 | 23 | 58 | 42 | 43 | 44 |
| OH4 | 80 | 76 | 62 | 26 | 25 | 27 | 58 | 42 | 43 | 44 |
| OE1 | 81 | 76 | 63 | 26 | 25 | 28 | 58 | 42 | 43 | 44 |
| 3.23 | 82 | 83 | | | | | | | | |
| 3.12 | 84 | 85 | | | | | | | | |

The term "epitope" refers to that portion of a molecule capable of being recognized by and bound by an antibody at one or more of the antibody's antigen-binding regions. Epitopic determinants usually consist of chemically active surface groupings of molecules such as amino acids or sugar side chains and usually have specific three dimensional structural characteristics, as well as specific charge characteristics. Preferably, the antibodies of the invention bind to an epitope on the N-terminus of mature hepcidin. More preferably, the antibodies of the invention bind to an epitope contained within amino acids 1 to 7, inclusive, of hepcidin-25. More preferably, the antibodies of the invention bind to the N-terminus of human hepcidin-25. Even more preferably, the antibodies of the invention bind to an epitope contained within amino acids 1 to 7, inclusive, of human hepcidin-25. Most preferably, the antibodies of the invention bind to an epitope contained within amino acids DTHFPIC of SEQ ID NO: 1.

The term "binding affinity ($K_D$)" as used herein, is intended to refer to the dissociation rate of a particular antigen-antibody interaction. The $K_D$ is the ratio of the rate of dissociation, also called the "off-rate ($k_{off}$)", to the rate of association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 µM indicates weak binding affinity compared to a $K_D$ of 1 nM. $K_D$ values may be obtained by methods known in the art.

The term "selective" used herein in reference to an anti-hepcidin-25 antibody of the invention refers to an antibody that binds hepcidin-25 with a $K_D$ about 1000-, 500-, 200-, 100-, 50-, 10-, or about 5-fold lower than the antibody binds at least one precursor form of hepcidin-25 and/or at least one N-terminally truncated form of hepcidin-25 present in the same mammalian species as measured by SPR at 25° C. Additionally, or alternatively, a hepcidin-25 selective antibody of the invention binds to hepcidin-25 but does not bind or only minimally binds to at least one precursor form of hepcidin-25 and/or at least one N-terminally truncated form of hepcidin-25 present in a mammalian species when assayed by the immunoassay and/or MALDI-TOF mass spectrometry methods described in Example 4-8 herein below. Preferably, the precursor form of hepcidin-25 is a pro-hepcidin, more preferably, human pro-hepcidin, and most preferably, human pro-hepcidin consisting of the amino acid sequence as shown in SEQ ID NO: 90. Preferably, the N-terminally truncated form of hepcidin-25 is human hepcidin-20 (i.e., amino acids 6-25 of SEQ ID NO:1) or human hepcidin-22 (amino acids 4-25 of SEQ ID NO:1).

The term "detect" or "detecting" is used in the broadest sense to include quantitative, semi-quantitative or qualitative measurements of a target molecule. In one aspect, methods described herein may only determine the presence or absence of a particular hepcidin polypeptide in a biological sample and, thus, that the hepcidin polypeptide is detectable or, alternatively, undetectable in the sample when assayed by the method.

The term "bioactivity," in reference to an antibody of the invention, includes, but is not limited to, epitope or antigen binding affinity, the in vivo and/or in vitro stability of the antibody, the immunogenic properties of the antibody, e.g., when administered to a human subject, and/or the ability to neutralize or antagonize a bioactivity of hepcidin-25, in vivo or in vitro, including, but not limited to, inhibition of serum iron level dysregulation in an animal model of inflammation, e.g., IL-6 induced inflammation challenge assay. The aforementioned properties or characteristics can be observed or measured using art-recognized techniques including, but not limited to, scintillation proximity assays, ELISA, ORIGEN immunoassay (IGEN), fluorescence quenching, fluorescence ELISA, competitive ELISA, SPR analysis including, but not limited to, SPR analysis using a BIAcore biosensor, in vitro and in vivo neutralization assays without limit (see, for example, PCT International Patent Application Publication No. WO 2006/062685).

The term "bioactivity" in reference to hepcidin includes, but is not limited to, specific binding of hepcidin to another protein including, but not limited to, its receptor ferroportin, one or more ferroportin-mediated functions of hepcidin, such as hepcidin-induced internalization and/or degradation of ferroportin (see, e.g., Nemeth, E., et al., Hepcidin Regulates Iron Efflux by Binding to Ferroportin and Inducing Its Internalization, *Science* 306, 2090-2093, (2004)), hepcidin regulation of ferroportin-mediated iron efflux, hepcidin induced decreases in serum iron levels, reticulocyte count, red blood cell count, hemoglobin, and/or hematocrit in a human, protein stability, i.e., hepcidin affecting the levels or activity of another protein in vivo or in vitro, and hepcidin expression levels and/or tissue distribution.

The term "inhibit" or "neutralize" as used herein with respect to a bioactivity of an antibody of the invention means the ability of the antibody to substantially antagonize, prohibit, prevent, restrain, slow, disrupt, eliminate, stop, reduce or reverse a bioactivity of hepcidin, including, but not limited to, a bioactivity of human, rat, or mouse hepcidin-25.

The terms "subject," and "patient," used interchangeably herein, refer to a mammal, preferably, a human. In certain embodiments, the patient has a disease, disorder, or condition that would benefit from a decreased level of hepcidin, a decrease in hepcidin bioactivity, and/or an increase in serum iron level, reticulocyte count, red blood cell count, hemoglobin, and/or hematocrit.

The term "specifically binds" as used herein in reference to the binding between an antibody and a hepcidin polypeptide means the antibody binds the hepcidin polypeptide with a $K_D$ less than about 500 nM as determined by SPR at 25° C.

In one embodiment, an antibody of the invention has a $K_D$ for human hepcidin-25 (SEQ ID NO: 1) less than about 100 nM, less than about 50 nM, less than about 25 nM, less than about 10 nM, less than about 5 nM, about 1 nM, or less than about 800 pM as determined by SPR at 25° C. Preferably, an antibody of the invention also specifically binds at least one mature hepcidin polypeptide of a non-human mammalian species, as determined by SPR at 25° C. More preferably, the antibody also specifically binds at least one hepcidin-25 polypeptide selected from the group consisting of mouse, rat and cynomolgus monkey hepcidin-25 (SEQ ID NOs: 3, 2, and 4, respectively), as determined by SPR at 25° C. Even more preferably, the antibody also specifically binds a cynomolgus monkey hepcidin-25 (SEQ ID NO: 4), as determined by SPR at 25° C. Even more preferably, the antibody also specifically binds mouse and/or rat hepcidin-25 (SEQ ID NOs: 3 and/or 2, respectively), as determined by SPR at 25° C.

In one embodiment, an antibody of the invention has a $K_D$ for human hepcidin-25 (SEQ ID NO: 1) less than about 100 nM, less than about 50 nM, less than about 25 nM, less than about 10 nM, less than about 5 nM, about 1 nM, or less than about 800 pM as determined by SPR at 25° C., and i) the antibody has a $K_D$ for human pro-hepcidin, human hepcidin-20 (SEQ ID NO:88) or human hepcidin-22 (SEQ ID NO:89) that is at least about 200-, about 100-, about 50-, about 10-, or about 5-fold higher, as determined by SPR at 25° C. or ii) binding of the antibody to human pro-hepcidin, human hepcidin-20 (SEQ ID NO:88) or human hepcidin-22 (SEQ ID NO:89) is not detectable or minimally detectable by the immunoassay and/or MALDI-TOF mass spectrometry methods described in Examples 4-7. Preferably, the antibody also specifically binds at least one mature hepcidin polypeptide of a non-human mammalian species, as determined by SPR at 25° C. More preferably, the antibody also specifically binds at least one hepcidin-25 polypeptide selected from the group consisting of mouse, rat and cynomolgus monkey hepcidin-25 (SEQ ID NOs: 3, 2 and 4, respectively), as determined by SPR at 25° C. Even more preferably, the antibody also specifically binds a cynomolgus monkey hepcidin-25 (SEQ ID NO: 4), as determined by SPR at 25° C. Even more preferably, the antibody also specifically binds mouse and/or rat hepcidin-25 (SEQ ID NOs: 2 and 3, respectively), as determined by SPR at 25° C.

In another embodiment, an antibody of the invention has a $K_D$ for human hepcidin-25 (SEQ ID NO: 1) between about 100 nM to about 800 pM, between about 50 nM to about 800 pM, between about 50 nM and about 1 nM, or between about 35 nM and 1 nM, as determined by SPR at 25° C., and i) the antibody has a $K_D$ for human pro-hepcidin, human hepcidin-20 (SEQ ID NO:88) or human hepcidin-22 (SEQ ID NO:89) that is at least about 200-, about 100-, about 50-, about 10-, or about 5-fold higher, as determined by SPR at 25° C. or ii) binding of the antibody to human pro-hepcidin, human hepcidin-20 (SEQ ID NO:88) or human hepcidin-22 (SEQ ID NO:89) is not detectable or minimally detectable by the immunoassay and/or MALDI-TOF mass spectrometry methods described in Examples 4-7. Preferably, the antibody also specifically binds at least one mature hepcidin polypeptide of a non-human mammalian species, as determined by SPR at 25° C. More preferably, the antibody also specifically binds at least one hepcidin-25 polypeptide selected from the group consisting of mouse, rat and cynomolgus monkey hepcidin-25 (SEQ ID NOs: 3, 2, and 4, respectively), as determined by SPR at 25° C. Even more preferably, the antibody also specifically binds a cynomolgus monkey hepcidin-25 (SEQ ID NO: 4), as determined by SPR at 25° C. Even more preferably, the antibody also specifically binds mouse and/or rat hepcidin-25 (SEQ ID NOs: 3 and 2, respectively), as determined by SPR at 25° C.

In one embodiment, an antibody of the invention has a $K_D$ for human hepcidin-25 (SEQ ID NO: 1) less than about 100 nM, less than about 50 nM, less than about 25 nM, less than about 10 nM, less than about 5 nM, about 1 nM, or less than about 800 pM as determined by SPR at 25° C. Preferably, an antibody of the invention also has a KD between about 100 nM to about 800 pM, between about 50 nM to about 800 pM, between about 50 nM and about 1 nM, or between about 35 nM and 1 nM for at least one mature hepcidin polypeptide of a non-human mammalian species, as determined by SPR at 25° C. More preferably, the antibody also has a KD between about 100 nM to about 800 pM, between about 50 nM to about 800 pM, between about 50 nM and about 1 nM, or between about 35 nM and 1 nM for at least one hepcidin-25 polypeptide selected from the group consisting of mouse, rat and cynomolgus monkey hepcidin-25 (SEQ ID NOs: 3, 2, and 4, respectively), as determined by SPR at 25° C. Even more preferably, the antibody also has a KD between about 100 nM to about 800 pM, between about 50 nM to about 800 pM, between about 50 nM and about 1 nM, or between about 35 nM and 1 nM for a cynomolgus monkey hepcidin-25 (SEQ ID NO: 4), as determined by SPR at 25° C. Even more preferably, the antibody also has a KD between about 100 nM to about 800 pM, between about 50 nM to about 800 pM, between about 50 nM and about 1 nM, or between about 35 nM and 1 nM for mouse and/or rat hepcidin-25 (SEQ ID NOs: 3 and 2, respectively), as determined by SPR at 25° C.

In another embodiment, an antibody of the invention has a $K_D$ for human hepcidin-25 (SEQ ID NO: 1) between about 100 nM to about 800 pM, between about 50 nM to about 800 pM, between about 50 nM and about 1 nM, or between about 35 nM and 1 nM, as determined by SPR at 25° C. Preferably, an antibody of the invention also has a KD between about 100 nM to about 800 pM, between about 50 nM to about 800 pM, between about 50 nM and about 1 nM, or between about 35 nM and 1 nM for at least one mature hepcidin polypeptide of a non-human mammalian species, as determined by SPR at 25° C. More preferably, the antibody also has a KD between about 100 nM to about 800 pM, between about 50 nM to about 800 pM, between about 50 nM and about 1 nM, or between about 35 nM and 1 nM for at least one hepcidin-25 polypeptide selected from the group consisting of mouse, rat and cynomolgus monkey hepcidin-25 (SEQ ID NOs: 3, 2 and 4, respectively), as determined by SPR at 25° C. Even more preferably, the antibody also has a KD between about 100 nM to about 800 pM, between about 50 nM to about 800 pM, between about 50 nM and about 1 nM, or between about 35 nM and 1 nM for a cynomolgus monkey hepcidin-25 (SEQ ID NO: 4), as determined by SPR at 25° C. Even more preferably, the antibody also has a KD between about 100 nM to about 800 pM, between about 50 nM to about 800 pM, between about 50 nM and about 1 nM, or between about 35 nM and 1 nM for mouse and/or rat hepcidin-25 (SEQ ID NOs: 3 and 2, respectively), as determined by SPR at 25° C.

In one embodiment, an antibody of the invention has a $K_D$ for human hepcidin-25 (SEQ ID NO: 1) less than about 100 nM, less than about 50 nM, less than about 25 nM, less than about 10 nM, less than about 5 nM, about 1 nM, or less than about 800 pM as determined by SPR at 25° C. and i) the antibody has a $K_D$ for human pro-hepcidin, human hepcidin-20 (SEQ ID NO:88) or human hepcidin-22 (SEQ ID NO:89) that is at least about 200-, about 100-, about 50-, about 10-, or about 5-fold higher, as determined by SPR at 25° C. or ii) binding of the antibody to human pro-hepcidin, human hepcidin-20 (SEQ ID NO:88) or human hepcidin-22 (SEQ ID NO:89) is not detectable or minimally detectable by the immunoassay and/or MALDI-TOF mass spectrometry methods described in Examples 4-7. Preferably, the antibody also has a $K_D$ between about 100 nM to about 800 pM, between about 50 nM to about 800 pM, between about 50 nM and about 1 nM, or between about 35 nM and 1 nM for at least one mature hepcidin polypeptide of a non-human mammalian species, as determined by SPR at 25° C. More preferably, the antibody also has a $K_D$ between about 100 nM to about 800 pM, between about 50 nM to about 800 pM, between about 50 nM and about 1 nM, or between about 35 nM and 1 nM for at least one hepcidin-25 polypeptide selected from the group consisting of mouse, rat and cynomolgus monkey hepcidin-25 (SEQ ID NOs: 3, 2 and 4, respectively), as determined by SPR at 25° C. Even more preferably, the antibody also has a $K_D$ between about 100 nM to about 800 pM, between about 50 nM to about 800 pM, between about 50 nM and about 1 nM, or between about 35 nM and 1 nM for a cynomolgus monkey hepcidin-25 (SEQ ID NO: 4), as determined by SPR at 25° C. Even more preferably, the antibody also has a $K_D$ between about 100 nM to about 800 pM, between about 50 nM to about 800 pM, between about 50 nM and about 1 nM, or between about 35 nM and 1 nM for mouse and/or rat hepcidin-25 (SEQ ID NOs: 3 and 2, respectively), as determined by SPR at 25° C.

In another embodiment, an antibody of the invention has a $K_D$ for human hepcidin-25 (SEQ ID NO: 1) between about 100 nM to about 800 pM, between about 50 nM to about 800 pM, between about 50 nM and about 1 nM, or between about 35 nM and 1 nM, as determined by SPR at 25° C., and i) the antibody has a $K_D$ for human pro-hepcidin, human hepcidin-20 (SEQ ID NO:88) or human hepcidin-22 (SEQ ID NO:89) that is at least about 200-, about 100-, about 50-, about 10-, or about 5-fold higher, as determined by SPR at 25° C. or ii) binding of the antibody to human pro-hepcidin, human hepcidin-20 (SEQ ID NO:88) or human hepcidin-22 (SEQ ID NO:89) is not detectable or minimally detectable by the immunoassay and/or MALDI-TOF mass spectrometry methods described in Examples 4-7. Preferably, the antibody also has a KD between about 100 nM to about 800 pM, between about 50 nM to about 800 pM, between about 50 nM and about 1 nM, or between about 35 nM and 1 nM for at least one mature hepcidin polypeptide of a non-human mammalian species, as determined by SPR at 25° C. More preferably, the antibody also has a KD between about 100 nM to about 800 pM, between about 50 nM to about 800 pM, between about 50 nM and about 1 nM, or between about 35 nM and 1 nM for at least one hepcidin-25 polypeptide selected from the group consisting of mouse, rat and cynomolgus monkey hepcidin-25 (SEQ ID NOs: 3, 2 and 4, respectively), as determined by SPR at 25° C. Even more preferably, the antibody also has a KD between about 100 nM to about 800 pM, between about 50 nM to about 800 pM, between about 50 nM and about 1 nM, or between about 35 nM and 1 nM for a cynomolgus monkey hepcidin-25 (SEQ ID NO: 4), as determined by SPR at 25° C. Even more preferably, the antibody also has a KD between about 100 nM to about 800 pM, between about 50 nM to about 800 pM, between about 50 nM and about 1 nM, or between about 35 nM and 1 nM for mouse and/or rat hepcidin-25 (SEQ ID NOs: 3 and 2, respectively), as determined by SPR at 25° C.

Antibody Expression

Standard molecular biology techniques are used to prepare the recombinant expression vector, transfect the host cells, select for transformants, isolate host cell lines producing an antibody of the invention, culture these host cells and recover the antibody from the culture medium.

The present invention is also directed to host cells that express an anti-hepcidin antibody of the invention. A wide variety of host expression systems known in the art can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably linked in one vector or, alternatively, the heavy chain and the light chain may be expressed independently from different promoters to which they are operably linked in two vectors—one expressing the heavy chain and one expressing the light chain. Optionally, the heavy chain and light chain may be expressed in different host cells.

Host cells can also be used to produce portions, or fragments, of intact antibodies, e.g., Fab fragments or scFv molecules, by techniques that are conventional. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to human hepcidin-25. The molecules expressed from such truncated DNA molecules are also encompassed by the antibodies of the invention.

The invention provides a host cell comprising a nucleic acid molecule of the present invention. Preferably, a host cell of the invention comprises one or more vectors or constructs comprising a nucleic acid molecule of the present invention. For example, a host cell of the invention is a cell into which a vector of the invention has been introduced, said vector comprising a polynucleotide encoding a LCVR of an antibody of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes.

Once expressed, the intact antibodies, individual light and heavy chains, or other immunoglobulin forms of the present invention can be purified according to standard procedures of the art, including ammonium sulfate precipitation, ion exchange, affinity (e.g., Protein A), reverse phase, hydrophobic interaction column chromatography, hydroxylapatite chromatography, gel electrophoresis, and the like. Substantially pure immunoglobulin of at least about 90%, about 92%, about 94% or about 96% homogeneity are preferred, and about 98 to about 99% or more homogeneity most preferred, for pharmaceutical uses. Once purified, partially or to homogeneity as desired, the sterile antibodies may then be used therapeutically, as directed herein.

Human Engineered Antibody

Preferably, an antibody of the invention to be used for therapeutic purposes, has the sequence of the framework and constant region (to the extent it exists in the antibody) derived from human so as to decrease the possibility that the antibody would elicit an immune response. Human engineered antibodies are of particular interest since they are valuable for therapeutic application and diminish the likelihood of a human anti-mouse antibody response frequently observed with antibodies of murine origin or antibodies comprising portions which are of murine origin when administered to a human subject. Preferably injected human engineered antibodies antibodies may have a half-life more like that of naturally occurring human antibodies than do e.g., murine antibodies, thereby allowing smaller and less frequent doses to be administered to a subject.

The term "human engineered antibodies" as used herein refers to an antibody wherein at least one portion is of human origin. For example, the human engineered antibody can comprise portions derived from an antibody of nonhuman origin, such as a mouse, and portions derived from an antibody of human origin, joined together, e.g., chemically by conventional techniques (e.g., synthetic) or prepared as a contiguous polypeptide using genetic engineering techniques.

Preferably, a "human engineered antibody" has CDRs that originate from or are derived from a parent antibody, i.e., a non-human antibody, preferably a mouse Mab or fragment thereof such as the mouse Fab 4C11, while framework and constant region, to the extent it is present, (or a significant or substantial portion thereof, i.e., at least about 90%, 92%, 94%, 95%, 96%, 97%, 98% or 99%) are encoded by nucleic acid sequence information that occurs in the human germline immunoglobulin region (see, e.g., the International ImMunoGeneTics Database) or in recombined or mutated forms thereof whether or not said antibodies are produced in a human cell. Preferably, at least two, three, four, five or six CDRs of a human engineered antibody are optimized from the CDRs of a non-human parent antibody from which the human engineered antibody was derived, to generate a desired property, e.g., improved specificity, affinity or neutralization, which may be identified by a screening assay, e.g., an ELISA assay. Preferably an optimized CDR in an antibody of the invention comprises at least one amino acid substitution when compared to that present in the parent mouse Fab 4C11, 3A9, or 5E8. Certain amino acid substitutions in the CDRs of human engineered antibodies of the invention as compared to those of the parent mouse Fab 4C11, 3A9 or 5E8 decrease the likelihood of instability of the antibody (e.g., removal of one or more CDR Asn residues) or decrease the likelihood of immunogenicity of the antibody when administered to a human subject (e.g., as predicted by IMMUNOFILTER™ Technology (Xencor, Inc., Monrovia, Calif.).

Human engineered antibodies preferably contain minimal sequence derived from a non-human antibody. Human engineered_antibodies may comprise residues which are found neither in the recipient antibody nor in the CDR or framework sequences imported from the parent antibody. Human engineered antibodies may be subjected to in vitro mutagenesis using methods of routine use in the art and, thus, the framework region amino acid sequences of the HCVR and LCVR regions of the human engineered recombinant antibodies are sequences that, while derived from those related to human germline HCVR and LCVR sequences, may not naturally exist within the human antibody germline repertoire in vivo. It is contemplated that such amino acid sequences of the HCVR and LCVR framework regions of the human engineered recombinant antibodies are at least about 85%, about 90%, about 92%, about 94%, about 95%, about 96%, about 98% or, more preferably, at least about 99% or, most preferably, 100% identical to a human germline sequence.

In preferred embodiments, a human engineered antibody of the present invention comprises human germline light chain framework sequences and human germline heavy chain framework sequences (see, e.g., PCT WO 2005/005604).

There are multiple methods available in the art to generate human engineered antibodies (see, e.g., PCT International Patent Application Publication WO2006/06046935; Queen, et al., Proc. Natl. Acad. Sci. USA 88:2869 (1991); Jones et al., Nature, 321:522 (1986); Riechmann, et al., Nature, 332:323-327 (1988); and Verhoeyen, et al., Science, 239:1534 (1988)). For example, human engineered antibodies may be produced by obtaining nucleic acid sequences encoding the HCVR and LCVR of a parent antibody (e.g., a murine antibody or antibody made by a hybridoma) which selectively binds hepcidin-25, identifying the CDRs in said HCVR and LCVR (non-human), and grafting such CDR-encoding nucleic acid sequences onto selected human framework-encoding nucleic acid sequences. Optionally, a CDR region may be optimized by mutagenizing randomly or at particular locations in order to substitute one or more amino acids in the CDR with a different amino acid prior to grafting the CDR region into the framework region. Alternatively, a CDR region may be optimized subsequent to insertion into the human framework region using methods available to one of skill in the art.

After the CDR-encoding sequences are grafted onto the selected human framework encoding sequences, the resultant DNA sequences encoding the human engineered variable heavy and variable light sequences are then expressed to produce a human engineered antibody that binds hepcidin-25. The human engineered HCVR and LCVR may be expressed as part of a whole anti-hepcidin-25 antibody molecule, i.e., as a fusion protein with human constant domain sequences. However, the HCVR and LCVR sequences can also be expressed in the absence of constant sequences to produce a human engineered anti-hepcidin-25 Fv or Fab, for example (see, e.g., Watkins, J., et al., Anal. Biochem. 253:37-45 (1997) and Watkins, J., et al., Anal. Biochem. 256:169-177, (1998)).

Diagnostic Uses

The antibodies of the present invention provide the means to accurately detect or determine the amounts of hepcidin-25 in a tissue or biological fluid for assessment of predispositions to hepcidin-25 promoted diseases and conditions, and for detection and diagnosis of such diseases and conditions in patients suffering there from. For example, the hepcidin-25 selective antibodies of the invention can be incorporated into sensitive and reliable immunoassays such as ELISA, RIA, immunodiffusion assays, or immuno-detection assays, such as SPR assays. Similarly, the hepcidin-25 selective antibodies of the present invention are also useful for immunohistochemical (IHC) and immunofluorescence (IF) assays of tissue or biological fluid samples. Such analyses can be used to detect aberrant levels of hepcidin-25 and hence to diagnose hepcidin-25 promoted diseases and conditions. More specifically, the present invention provides methods of diagnosing a hepcidin-25 associated disease or condition in a patient by determining the level of hepcidin-25 in a sample of tissue or a biological fluid from the patient and comparing the level of hepcidin-25 in the sample with the level of hepcidin-25 in a corresponding sample from one or more control individuals or with a reference standard thereby detecting a disease state associated with the anomalous level of hepcidin-25. The disease state may comprise one or more of a genetic or non-genetic disease associated with decreased serum iron levels, reticulocyte count, red blood cell count, hemoglobin, and/or hematocrit. Preferably the disease state may comprise one or more of a genetic or non-genetic disease associated with anemia.

A method of monitoring a hepcidin-25 associated disease or condition in a patient is also provided. The method includes determining the level of hepcidin-25 in a sample of a tissue or biological fluid from a patient suffering from or at risk of a hepcidin-25 associated disease or condition at a first time point; determining the level of hepcidin-25 in one or more samples of tissue or biological fluid from the patient at one or more different time points; comparing the levels of hepcidin-25 determined at different time points and thereby monitoring the hepcidin-25 promoted disease or condition.

The hepcidin-25 selective antibodies of the present invention are particularly useful when applied to high-throughput methods. Such methods include micro-chip and micro-array methods, such that many samples can be tested on a microplate or slide, or other assay substrate known in the art.

The presence of hepcidin-25 or levels thereof in a biological sample may be established by combining the biological sample with, e.g., an antibody of the invention under conditions suitable to form an antigen-antibody complex. The antibody is directly or, more preferably, indirectly labeled with a detectable moiety to facilitate detection of the bound or unbound antibody. A wide variety of methods of detection of immunocomplex formation are well known in the art, for example, ELISA, RIA, immunoblot (e.g., dot blot, slot blot, western blot, etc.), indirect immunofluorescence techniques and methods that rely on detection of changes in physical parameters, such as for instance, SPR, and the like. Such applications include methods that utilize a hepcidin-25 selective antibody of the invention conjugated with a detectable moiety to detect hepcidin in a biological sample, e.g., in a human biological fluid or in a cell or tissue extract. Antibodies of the invention may be used in such assays with or without modification with a detectable moiety. If modified with a detectable moiety, antibodies of the invention may be modified by covalent or non-covalent attachment of the detectable moiety. As used herein, the term "detectable" describes a feature of a substance (a conjugate, compound, or moiety) that allows identifying or tracing the substance by a detector, using known analytical techniques. Representative examples of detectable moieties include, without limitation, chromophores, fluorescent moieties, phosphorescent moieties, luminescent moieties, radioactive moieties, various enzymes (such as alkaline phosphatase, or horseradish peroxidase), magnetic moieties (e.g., diamagnetic, paramagnetic and ferromagnetic materials), and heavy metal clusters, as well as any other known detectable moieties. The amount of an antibody-antigen standard complex formed may be quantitated by various methods known in the art, such as, e.g., photometric or colorimetric means. Preferably, the antibodies of the invention are used without modification, i.e., indirectly labeled, according to methods well known in the art.

The invention embodies a method for detecting hepcidin-25 protein in a biological sample, comprising incubating an antibody of the invention with a biological sample under conditions and for a time sufficient to permit said antibody to bind to hepcidin-25 protein, and detecting said binding. Preferably, the antibody is 5E8, OH4 and/or OB3. A preferred method for detecting hepcidin-25 protein in a biological sample is a sandwich ELISA, comprising incubating a first antibody of the invention with the biological sample under conditions and for a time sufficient to permit said antibody to bind to hepcidin-25 protein, removing unbound sample, applying a second antibody that selectively binds an epitope contained within amino acids 1 to 7 of SEQ ID NO: 1, removing unbound second antibody, and detecting binding of said second antibody. Preferably, the first antibody is 3.23 or 3.12 and the second antibody is OH4 or OB3. Anti-hepcidin Mab 3.23 comprises two light chain polypeptides and two heavy chain polypeptides wherein each of the light chain polypeptides have the amino acid sequence as shown in SEQ ID NO: 82 and each of the heavy chain polypeptides have the amino acid sequence as shown in SEQ ID NO: 83 and binds a polypeptide having the amino acid sequence as shown in SEQ ID NO: 1. Anti-hepcidin Mab 3.12 comprises two light chain polypeptides and two heavy chain polypeptides wherein each of the light chain polypeptides have the amino acid sequence as shown in SEQ ID NO: 84 and each of the heavy chain polypeptides have the amino acid sequence as shown in SEQ ID NO: 85 and binds a polypeptide having the amino acid sequence as shown in SEQ ID NO: 1. A more preferred method for detecting hepcidin-25 protein in a biological sample is a sandwich ELISA, comprising incubating a first antibody that specifically binds an epitope contained within amino acids 5-25 of hepcidin with the biological sample under conditions and for a time sufficient to permit said antibody to bind to hepcidin protein(s), removing unbound sample, applying a second antibody that binds an epitope contained within amino acids 1 to 7 of hepcidin-25, removing unbound second antibody, and detecting the presence or absence of binding of said second antibody. Preferably, the first antibody is 3.23 or 3.12 and the second antibody is OH4 or OB3. More preferably, the second antibody is not labeled and the binding is detected indirectly according to methods known in the art.

The present invention also provides compositions, methods and kits for screening samples suspected of containing hepcidin-25. Such screening may be performed on patient samples, or laboratory samples suspected of containing or producing such a polypeptide. A kit can contain a hepcidin-25 selective antibody of the present invention. The kit can contain a suitable buffer and reagents for detecting an interaction between a sample and a hepcidin-25 selective antibody of the present invention. The provided reagent can be radiolabeled, fluorescently-labeled or enzymatically-labeled agent capable of binding or interacting with an antibody of the present invention such as an anti-mouse IgG antibody.

The reagent of the kit can be provided as a liquid solution, attached to a solid support or as a dried powder. When the reagent is provided in a liquid solution, preferably, the liquid solution is an aqueous solution. Preferably, when the reagent provided is attached to a solid support, the solid support can be chromatographic media, a test plate having a plurality of wells, or a microscope slide. When the reagent provided is a dry powder, the powder can be reconstituted by the addition of a suitable solvent, which may be provided in the kit as well.

The kit of the invention is provided in a container that generally includes a vial into which the antibody, antigen or detection reagent may be placed, and preferably suitably aliquotted. The kits of the present invention will also typically include a means for containing the antibody, antigen, and reagent containers for commercial sale. Such containers may include plastic containers into which the desired vials are retained and one or more necessary chemicals, such as chromatography material, solvents and eluents, test tubes, detergents, antibodies and chemicals for the detection reaction.

Therapeutic Uses

Hepcidin-25 promoted diseases or conditions may be prevented or treated by administering to a patient in need thereof a pharmaceutical composition including a hepcidin-25 selective antibody a second antibody that binds an epitope contained within amino acids 1 to 7, inclusive, of (1) human hepcidin-25, i.e., DTHFPIC (SEQ ID NO: 5), and/or (2) mouse hepcidin-25, i.e., DTNFPIC (SEQ ID NO: 86).

A pharmaceutical composition comprising an antibody of the invention may be used to increase serum iron levels, reticulocyte count, red blood cell count, hemoglobin, and/or hematocrit in a human when an effective amount is administered to a human subject in need thereof. Furthermore, an antibody of the invention may be useful for the treatment of conditions, diseases, or disorders wherein the presence of hepcidin-25 causes or contributes to undesirable pathological effects or a decrease of hepcidin-25 levels or hepcidin bioactivity has a therapeutic benefit in human subjects. Such conditions, diseases or disorders include anemia including, but not limited to, anemia resulting from infection, inflammation, chronic disease, and cancer. Subjects may be male or female. Preferably, a human subject has or is at risk of having undesirably low serum iron level, low reticulocyte count, red blood cell count, hemoglobin, and/or hematocrit. More preferably, a human subject is at risk for, or suffering from, anemia including, but not limited to, anemia resulting from infection, inflammation, chronic disease, and/or cancer.

Additionally, the use of an antibody of the invention for use in the manufacture of a medicament for the treatment or prevention of anemia including, but not limited to, anemia resulting from infection, inflammation, chronic disease, and cancer.

The hepcidin-25 selective antibodies of the present invention are also useful for prevention and therapy of hepcidin-25 promoted diseases and conditions. The anti-hepcidin-25 selective Mabs of the invention can be formulated in pharmaceutical compositions for passive immunization against hepcidin-25. Functional fragments of the MAbs of the present invention, such as, for instance Fab fragments, F(ab') 2 fragments and any fragments that retain the ability to selectively bind hepcidin-25 can also be incorporated into pharmaceutical compositions and applied in therapy.

Furthermore, the hepcidin-25 selective Mabs of the present invention can be applied in immunoassays for monitoring the progression of hepcidin-25 promoted diseases and conditions, where the level or amount of hepcidin-25 provides an indication of the success of treatment or therapy, or of progression of the disease or condition.

Moreover, the Mabs of the present invention are useful in methods of evaluating a hepcidin-25 blocking treatment of a patient suffering from a hepcidin-25 promoted disease or condition. The method includes the steps of:

a) obtaining a first sample of biological fluid from the patient prior to or in the early stages of a treatment;

b) determining the level of hepcidin-25 in the first sample by an immunoassay method;

c) obtaining a second sample of biological fluid from the patient after a suitable time within which the treatment would have an effect;

d) determining the amount of hepcidin-25 in the second sample by the immunoassay method, e) comparing the determined amounts of hepcidin-25 in the first sample with the amount of hepcidin-25 in the second sample so as to determine the efficacy of the hepcidin-25 binding or blocking treatment.

The above-described method applied to evaluating a hepcidin-25 binding treatment or blocking treatment in a patient is particularly valuable in clinical practice, where timing of decisions to proceed with one therapeutic regimen or another may be critical to the outcome for the patient. The method of the present invention provides information on which to base these critical decisions. The method provides a measurement of the hepcidin-25 amount prior to or in the early stages of treatment and provides one or more measurements of hepcidin-25 at one or more periods after initiation of treatment, particularly when the treatment is expected to have begun to be effective.

The hepcidin-25 blocking treatment may be passive administration of anti-hepcidin-25 selective antibody to a patient. The anti-hepcidin-25 selective antibody may be a chimeric human/non-human antibody, a humanized or a fully human monoclonal anti-hepcidin-25 selective antibody, or any hepcidin-25 selective antibody fragment that is functional in binding hepcidin-25.

A wide variety of methods of detection of immunocomplex formation are well known in the art, for example, ELISA, RIA, immunoblot (e.g., dot blot, slot blot, western blot etc.), indirect immunofluorescence techniques and methods that rely on detection of changes in physical parameters, such as SPR. In one widely used method immuno-complex formation is detected through the use of a label, such as a radiolabel or an enzyme tag (such as alkaline phosphatase or horseradish peroxidase). Additional advantages may accrue through the use of a secondary binding ligand such as a second antibody or an avidin-coupled molecule for binding a biotinylated ligand, according to methods well known in the art.

The terms "treatment" and "treating" as used herein refers to administering a substance to a patient, who has a disease, condition, or disorder described herein, a symptom of such a disease, condition, or disorder or a predisposition toward such a disease, condition, or disorder, with the purpose to confer a therapeutic effect, e.g., to cure, relieve, alter, affect, control, stop, ameliorate, or prevent the disease, condition, or disorder, a symptom of it, or a predisposition toward it. Preferably, the patient treated is a mammal, and, more preferably, a human. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation.

Pharmaceutical Composition

An antibody of the invention can be incorporated into a pharmaceutical composition suitable for administration to a human subject. An antibody of the invention may be administered to a human subject alone or in combination with a pharmaceutically acceptable carrier and/or diluent in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions can be designed in accordance with conventional techniques known in the art.

Suitable carriers for pharmaceutical compositions include any material which, when combined with a Mab of the invention, retains the molecule's activity and is non-reactive with the subject's immune system.

A pharmaceutical composition comprising an anti-hepcidin-25 Mab of the present invention can be administered to a subject at risk for or exhibiting pathologies as described herein, e.g., anemia disorders, using standard administration techniques.

The phrase "effective amount" as used herein refers to an amount necessary (at dosages and for periods of time and for the means of administration) to achieve the desired therapeutic result. An effective amount of the antibody may vary according to factors such as the disease state, age, sex, and weight of the individual, and the ability of the antibody or antibody portion to elicit a desired response in the individual. An effective amount is also one in which any toxic or detrimental effect of the antibody, are outweighed by the therapeutically beneficial effects.

An effective amount is at least the minimal amount, but less than a toxic amount, of an active agent which is necessary to impart therapeutic benefit to a subject. Stated another way, an effective amount or therapeutically effective amount of an antibody of the invention is an amount which in mammals, preferably, humans, (i) increases serum iron levels, reticulocyte count, red blood cell count, hemoglobin, and/or hematocrit, or (ii) treats a condition, disorder or disease wherein the presence of hepcidin-25 causes or contributes to an undesirable pathological effect, or (iii) a decrease in hepcidin-25 levels or hepcidin bioactivity results in a beneficial therapeutic effect in a mammal, preferably, a human, including, but not limited to, anemia including, but not limited to, anemia of chronic disease, including, but not limited to, anemia resulting from infection, inflammation, chronic disease, and/or cancer. An effective amount of an antibody of the invention may be administered in a single dose or in multiple doses. Furthermore, an effective amount of an antibody of the invention may be administered in multiple doses of amounts that would be less than an effective amount if not administered more than once.

As is well known in the medical arts, dosages for any one subject depends upon many factors, including, frequency and route of administration, general health, and other drugs being administered concurrently. Dose may further vary depending on the type and severity of the disease. A typical dose can be, for example, in the range of about 0.1 to about 100 mg; preferably, about 1 to about 100 mg; more preferably, about 5 to about 50 mg; however, doses below or above this exemplary range are envisioned, especially considering the aforementioned factors. A daily parenteral dosage regimen can be about 10 µg/kg to about 10 mg/kg of total body weight, preferably from about 100 µg/kg to about 10 mg/kg, more preferably from about 1 mg/kg to about 10 mg/kg. Progress may be monitored by periodic assessment, and the dose adjusted accordingly.

These suggested amounts of antibody are subject to a great deal of therapeutic discretion. The key factor in selecting an appropriate dose and scheduling is the result obtained. Factors for consideration in this context include the particular disorder being treated, the clinical condition of the individual patient, the cause of the disorder, the site of delivery of the antibody, the particular type of antibody, the method of administration, the scheduling and frequency of administration, and other factors known to medical practitioners.

The route of administration of an antibody of the present invention may be oral, parenteral, by inhalation, or topical. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Parenteral delivery by intravenous or intraperitoneal or subcutaneous injection is preferred. Subcutaneous injection is most preferred. Suitable vehicles for such injections are well known in the art.

The pharmaceutical composition typically must be sterile and stable under the conditions of manufacture and storage in the container provided, including e.g., a sealed vial, syringe or other delivery device, e.g., a pen. Therefore, pharmaceutical compositions may be sterile filtered after making the formulation, or otherwise made microbiologically acceptable.

The following examples are offered for illustrative purposes only, and are not intended to limit the scope of the present invention.

EXAMPLES

Example 1

Production of Human Hepcidin-25

Human hepcidin-25 can be obtained from commercial sources (e.g., Peptide International (Louisville, Ky.)) or produced by a variety of synthetic or recombinant techniques known in the art. For example, a fusion protein comprising the twenty-five amino acids of hepcidin-25 and having the amino acid sequence as shown in SEQ ID NO: 95 is expressed in $E.\ coli$. Inclusion bodies are isolated from 3 liters of $E.\ coli$ expressing the human hepcidin-25 fusion protein after a 3-6 hour induction with 1 mM IPTG at 37° C. The inclusion bodies are solubilized in buffer A (50 mM Tris and 8 M urea (pH 8.0)). The supernatant is passed over an Immobilized Metal-Ion Affinity Chromatography (IMAC) column (20 mL resin). The column is washed with buffer A until the absorbance returned to baseline and the bound polypeptides are batch eluted from the column by 0.5 M imidazole in buffer A. The human hepcidin-25 fusion protein is pooled and reduced with 50 mM DTT. This fusion protein is then refolded by diluting pooled material into 2 M urea, 3 mM cysteine, 50 mM Tris (pH 8.0) to a final protein concentration less than 50 µg/mL. This material is stirred at room temperature and air oxidized for 48 hours. The oxidized polypeptides are passed over an IMAC column (20 mL) at a flow rate of 5 mL/min, and the human hepcidin-25 fusion protein is batch eluted from the column by 0.5 M imidazol in buffer A. The pooled fractions containing the human hepcidin-25 fusion protein are concentrated and passed through a sizing column (e.g., SUPERDEX® 75, GE Healthcare, XK26/60) equilibrated with 50 mM Tris, 4 M urea, pH 8.0, at a flow rate of 3 mL/min. Eluted monomeric fusion protein is pooled and then diluted to 50 mM Tris, 2M urea, 5 mM $CaCl_2$, pH 8.0 and then is cleaved with enterokinase to produce human hepcidin-25 of SEQ ID NO: 1. Uncleaved human hepcidin-25 fusion protein is removed by passive IMAC chromatography (as outlined above). The flow-through from the IMAC column is then loaded onto a C-18 Reversed Phase column at a flow rate of 4.0 mL/minute. The column is washed with 0.1% TFA in water until the absorbance returns to baseline and the bound polypeptides are eluted from the column with a linear gradient of ACN from 20% to 40% with 0.1% TFA at a rate of 0.5%/min. Fractions which contain the human hepcidin-25 polypeptide are pooled and analyzed by N-terminal amino acid sequencing and matrix assisted laser desorption/ionization mass spectrometry (MALDI-MS).

Polypeptides encoding rat, mouse, and cynomolgous monkey hepcidin-25 and various N-terminally truncated forms of human hepcidin-25, including hepcidin-22 and hepcidin-20 were also made essentially as described for human hepcidin-25.

Example 2

Production of N-Terminal Hepcidin-25 Antibodies

Mice are immunized with a N-terminal hepcidin peptide (amino acids 1-7 of SEQ ID NO: 1) conjugated with a five amino acid peptide linker (i.e., GPGPG) to an OVA peptide (amino acids 323-336) sequence, i.e., full-length immunogen DTHFPICGPGPGISQAVHAAHAEINE (SEQ ID NO:87) and the spleens from these mice are harvested at Day 27. The B-cells are sorted at 1 cell per well for $Ag^+$ and $IgG^+$ memory and germinal center cells and are co-cultured with EL4B cells for 2 weeks. The resulting IgG containing supernatants are then diluted 1.4 fold and screened in the following three ELISA formats: 1) 96 well plates coated with NEUTRAVIDIN™ binding protein, a deglycosylated and isoelectrically neutral form of avidin (Pierce Biotechnology, Rockville, Ill.), at 2 µg/mL in carbonate buffer overnight. Nonspecific binding sites are blocked with caseine for 1 hour. The plate is then washed 3 times with PBS with 0.05% Tween-20 and 100 nM biotinylated hepcidin is incubated on plate for 1 hour. The plate is washed again as described. IgG supernatants from culture are then incubated for 1 hour and the plate is washed. Specific binding of hepcidin-25 antibody is detected by 0.5 µg/mL goat anti-mouse IgG Fcγ-alkaline phosphatase. Alkaline phosphatase activity is measured by adding an appropriate amount of PMP/AMP substrate (6 mg/ml phenolphthalein monophosphate (PMP) in 0.5 M Tris, pH 10.2, 2% 2-amino-2-methyl-1-propanol (AMP), 0.1% $NaN_3$) and the amount of absorbance at 560 nm is measured; 2) 96-well plates are coated with goat anti-mouse kappa IgG at 2 µg/ml in carbonate buffer overnight. Nonspecific binding sites are then blocked with caseine for 1 hour. The plate is washed 3 times with PBS with 0.05% Tween-20 and the IgG supernatants from the culture are incubated for 1 hour. Biotinylated hepcidin-25 (100 nM) is then incubated on the plate for 1 hour and the plate is washed as previously described. Specific binding of hepcidin-25 to captured antibody is then detected by adding 1 µg/ml NEUTRAVIDIN-AP™, a NEUTRAVIDIN™-alkaline phosphatase conjugate (Pierce Biotechnology, Rockford, Ill.) and detecting alkaline phosphatase activity by adding PMP/AMP substrate and measuring absorbance at 560 nm; and 3) 96-well plates are coated with 100 nM hepcidin-25 in water overnight at 37° C. Nonspecific binding sites are then blocked with caseine for 1 hour and the plate is washed 3 times with PBS with 0.05% Tween-20. IgG supernatants from the culture are then incubated for 1 hour and the plate is again washed as described. Specific binding of N-terminal hepcidin-25 antibody is detected by 0.5 µg/ml goat anti-mouse IgG Fcγ-alkaline phosphatase. Alkaline phosphatase activity is measured with PMP/AMP substrate and the amount of absorbance at 560 nm is measured.

B cells expressing mouse antibodies specific for the N-terminus of hepcidin-25 such as 3A9, 4C11 and 5E8 are then used to isolate RNA and the variable regions were amplified by RT-PCR and subsequently cloned into commercially available mouse IgG1 vectors or heavy and light chain respectively. The transiently expressed mouse antibodies were confirmed as N-terminal hepcidin-25 specific antibodies using SPR.

Example 3

Affinity Binding Measurements of Anti-Hepcidin Fabs and Mabs Using SPR

A SPR biosensor such as the BIAcore® T100 may be used to measure binding kinetics and affinity of antibodies such as the antibodies disclosed herein. The BIAcore® system utilizes the optical properties of SPR to detect alteration in protein concentration of interacting molecules within a dextran biosensor matrix. Except as noted, all reagents and materials are purchased from BIAcore® AB (Upsala, Sweden). All measurements are performed at 25° C. Samples are dissolved in HBS-EP buffer (150 mM sodium chloride, 3 mM EDTA, 0.05% (w/v) surfactant P-20, and 10 mM HEPES, pH 7.4). To capture Fabs with human kappa, goat-anti-human kappa is immobilized on flow cells 1 to 4 of a CM5 sensor chip at a level of 5000-10000 response units (Rus) using an amine coupling kit. To capture Mabs with mouse IgG1, goat-anti-mouse Fc gamma is immobilized on flow cells 1 to 4 of a CM5 sensor chip at a level of 5000-10000 Rus using an amine coupling kit. To capture antibodies with human IgG4, protein A is immobilized on flow cells 1 to 4 of a CM4 sensor chip at a level of 400-700 Rus using an amine coupling kit. Fabs prepared from *E. coli* periplasma and Mabs prepared from mammalian cell culture are evaluated using multiple analytical cycles. Each cycle consists of the following steps: 0.3-2 minutes injection of a Fab or a Mab at ~10 µL/minute aiming at a capture of 200-1000 Rus, 2 minutes injection at 50 µL/minute of various concentrations of human hepcidin-25 (from 600 nM to 0.1 nM) obtained as described in Example 1 above followed by 2-10 minutes for dissociation, and regeneration using 30 µL of 10 mM glycine hydrochloride, pH 1.5. The measurements are obtained at 25° C. and the association and dissociation rates for each cycle are evaluated using a "1:1 with mass transfer" binding model in the BIAevaluation software.

The mouse monoclonal antibodies 3A9, 4C11, 5E8, OB3, OH4, OB1, and OE1 exhibit binding to human hepcidin-25 with an affinity ($K_D$) from about 36 nM to about 1 nM. Mouse monoclonal antibody OH4 binds human hepcidin-25 with a $K_D$ of about 1.2 nM but does not detectably bind to human hepcidin-20 or human hepcidin-22. Mouse monoclonal antibody 5E8 binds human hepcidin-25 but does not detectably bind to mouse or rat hepcidin-25. Mouse monoclonal antibody 4C11 binds human, mouse, and rat hepcidin-25 and, to a much lesser degree, human hepcidin-22 (about 209 nM) but not human hepcidin-20.

Example 4

Identification of a Pair of Mabs that Bind Human Hepcidin-25 Simultaneously Monoclonal antibodies raised against amino acids 1-7, inclusive, of human hepcidin-25 which demonstrated high affinity binding to human hepcidin-25 by SPR analysis were tested for their ability to simultaneously bind to human hepcidin-25 with Mab 3.23.

Briefly, on a Biacore® T100, goat anti-mouse IgG1 Fc polyclonal antibody was immobilized onto flow cell 1 to 4 of CM5 chip at 5000-15000 response units (Ru). Mab 5E8 was captured on flow cell 2, Mab 4C11 was captured on flow cell 3, and Mab 3A9 was captured on flow cell 4. Flow cell 1 was used as a reference flow cell. All flow cells were then injected with human hepcidin-25. The flow cells with Mabs 5E8, 4C11, and 3A9 immobilized thereon all showed an increase in Rus, indicating binding of those Mabs to human hepcidin-25. Next, all of the flow cells were injected with Mab 3.23. Only flow cell 2, with Mab 5E8 immobilized thereon, showed simultaneous binding of human hepcidin-25 by Mabs 5E8 and 3.23.

Additionally, Mabs Hu22, 3.23, 3.12, and a negative control human IgG4 antibody were immobilized on separate flow cells of a Sensor Chip_CM4 chip (Biacore) at 1000-4000 Rus. The flow cells were then injected with human hepcidin-25. Next, the flow cells were injected with Mab 5E8. The flow cells having Mabs Hu22, 3.23, and 3.12 immobilized thereon showed binding of human hepcidin-25 and then simultaneous binding of Mab 5E8. The flow cell having the negative control human IgG4 immobilized thereon did not show binding to either human hepicin-25 or Mab 5E8. Furthermore, Mab 5E8 did not bind human hepcidin-25 simultaneously with either rabbit polyclonal antiserum raised to KLH conjugated peptides consisting of amino acids 1-7 of human and mouse hepcidin-25 (Alpha Diagnostic International, San Antonio Tex.; cat. #Hepc13-S) or an IgG purified preparation thereof (Alpha Diagnostic International; cat.#Hepc13-A)).

Example 5

Sandwich ELISA Assay for Measuring Human Hepcidin-25

The wells of a multi-well plate are coated for 1 hour at room temperature with Mab 3.23 at a concentration of 2 mg/L in carbonate-bicarbonate coating buffer, pH 9.40 (Pierce Biotechnology, Rockville, Ill.). Next, wells are aspirated and washed 3 times with TBST (TRIS buffered saline containing 10 mmol/L Tris pH 7.4, 150 mmol/L NaCl with 1 mL Tween-20/L). Wells are then blocked for 1 hour with TBS-casein blocking buffer (150 mM NaCl, 25 mM Tris, 1% casein, pH 7.4 with Kathon antimicrobial (Pierce Biotechnology; cat. #37532). Next, 100 µL of a hepcidin-25 standard (varying concentrations of synthesized human hepcidin-25 in assay buffer consisting of 50 mmol/L HEPES, pH 7.40, 150 mmol/L NaCl, 10 mL/L Triton® X-100 non-ionic surfactant (Union Carbide Corp., Danbury, Conn.), 5 mmol/L EDTA, and 5 mmol/L ethyleneglycotetraacetic acid (EGTA) is added to a set of the wells to generate a calibration curve. Thereafter, serum samples are diluted 1:20 in assay buffer and added to their respective wells, and the ELISA plate is allowed to incubate for 1 hour at room temperature. Following aspiration, wells are washed 3 times with TBST, and 100 µL of a 1:1000 dilution of biotinylated anti-hepcidin-25 Mab 5E8 at 1 mg/ml is added to the wells for 1-hour incubation at room temperature. Following aspiration, wells are washed 3 times with TBST, and 100 µL of a poly-streptavidin-HRP solution (Pierce Biotechnology, Rockville, Ill.) is added to the wells for a 30-min incubation at room temperature. The wells are then washed 3 times with TBST. After the last aspiration of TBST, 100 µL of 3,3',5,5'-tetramethylbenzidine development substrate (Pierce Biotechnology, Rockville, Ill.) is added to the wells and allowed to incubate for 30 min at room temperature. The reaction was stopped with an equal volume of 2 N phosphoric acid, and plates are read at 450 nm.

Serum concentrations of hepcidin-25 from 40 normal and cancer patients measured by the sandwich ELISA described above ranged from 5 to 656 µg/L and directly correlated with serum concentrations of hepcidin-25 measured using a standard LC/MS assay (r=0.98, p<0.0001)(see, Murphy, et al., (2007)). Also, 100 human serum samples from healthy donors (50 males and 50 females; age range between 18 to 66 years, mean 37 years) obtained from Bioreclamation, Inc.

(East Meadow, N.J.)) were determined to have hepcidin-25 concentrations ranging from <1-79 ng/ml. Additionally, the sandwich ELISA detected the human hepcidin-25 control peptide in a dose-dependent manner down to at least 1 ng/ml. On the other hand, neither the human hepcidin-25 control peptide (up to 2 ng/ml) nor endogenous hepcidin-25 in a human serum sample positive control, i.e., previously determined by LC/MS assay to contain hepcidin-25, is detectable in the same assay when Mab 5E8 was substituted with i) rabbit polyclonal antiserum raised to KLH conjugated peptides consisting of amino acids 1-7 of human and mouse hepcidin-25 (Alpha Diagnostic International, San Antonio Tex.; cat. #Hepc13-S) or ii) a IgG purified preparation thereof (Alpha Diagnostic International; cat.#Hepc13-A)). Further, neither the hepcidin-25 standard nor the human serum sample positive control were detectable when the HEPC-13-S antiserum or the IgG purified preparation thereof were i) coated on separate wells of the assay plate, i.e., as the capture antibodies, ii) added to the assay as biotin-conjugated detection antibodies, or iii) added to the assay as unconjugated detection antibodies, i.e., with their binding subsequently assayed for by use of a anti-rabbit IgG secondary antibody.

The human hepcidin-25 control peptide and endogenous hepcidin-25 in the human serum positive control sample was not detected when the sandwich ELISA was conducted using Mab 5E8 as the capture antibody and paired with a commercially available rabbit polyclonal IgG raised against a KLH conjugated, 13-amino acid mature human hepcidin C-terminal peptide (Alpha Diagnostic International, San Antonio, Tex.; cat. #HEPC12-A).

Example 6

Determination of Selectivity of Anti-Hepcidin Antibodies Using MALDI-TOF

Clinical routine diagnosis of biomarkers is mostly based on immunological, quantitative techniques—e.g., ELISA. These methods are often not applicable for small antigens or for antigen isoforms (Sparbier, K., International Meeting of the Association of Biomolecular Resource Facilities, Salt Lake City, Utah, Poster V28-S, (2008); and Gutierrez, J. A., et al., (2005)). Mabs or Fabs may be evaluated for their ability to selectively immunoprecipitate endogenous hepcidin-25, rather than precursors or truncated forms thereof, from human serum via MALDI-TOF mass spectrometry on antibody-bound hepcidin polypeptides performed after sample reduction.

Anti-human hepcidin Mabs or Fabs are coated onto separate wells of a 96-well standard ELISA plate in carbonate-bicarbonate (pH 9.4) buffer for 1 hour at room temperature at a concentration of 2 mg/L. The wells are then aspirated and washed 3 times with TBST. Human serum samples containing a known amount of hepcidin-25 (diluted in assay buffer) is added at 100 µl/well for one hour at room temperature. The wells are aspirated and washed 3 times with TBST. Captured hepcidin polypeptides are eluted by adding 40 µL/well of 0.1% formic acid for 5 minutes at room temperature. The eluted samples are collected and concentrated with a C4 ZipTip™ (Millipore, Billerica, Mass.), a 10 µL pipette tip with a bed of chromatography media for purifying and concentrating femtomoles to picomoles of protein or peptides, ideally ranging from 25,000 MW to 100,000 MW. One-half of a microliter of sample is spotted onto a MALDI target and an equal volume of matrix solution (50% acetonitrile, 0.1% TFA saturated with alpha-cyan-4-hydroxycinnamic acid) is added to the sample. The sample is dried and analyzed with a 4700 TOF-TOF Mass Spectrometer (Applied Biosystems) operated in the linear mode.

Figure 2:
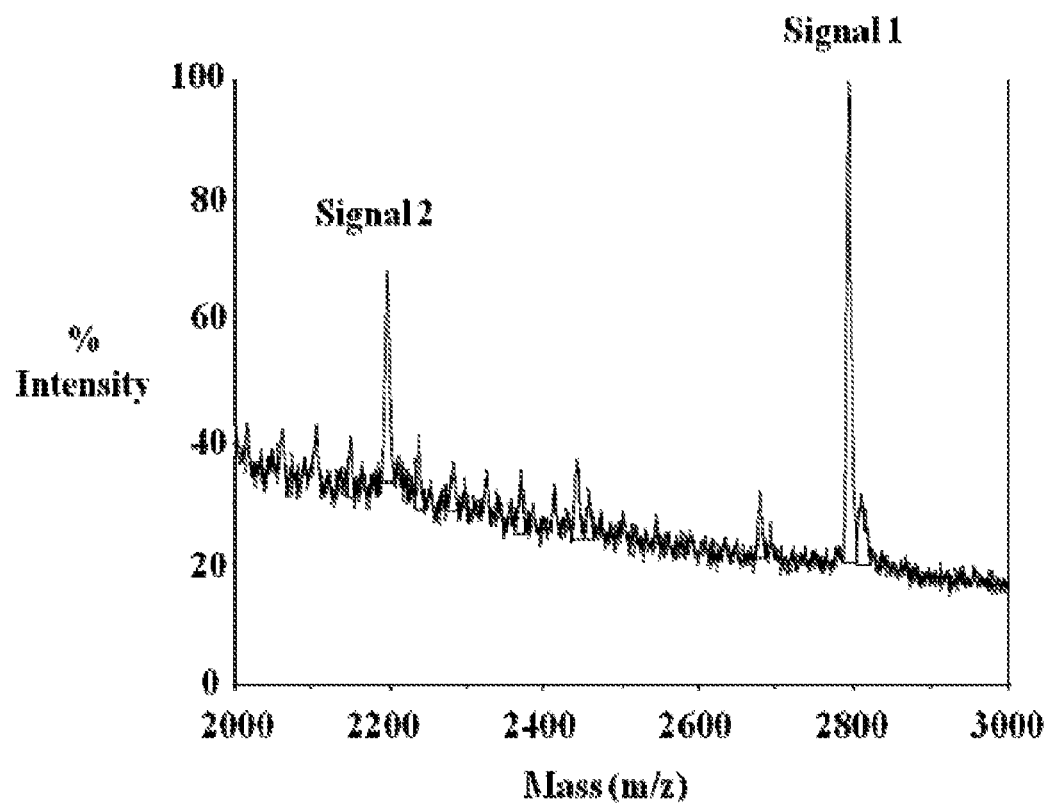
FIG. 2 depicts a magnified view of the mass spectrum shown in FIG. 1 in a relevant region (MW 2000-3000 Da). As the chromatogram demonstrates, the Mab 3.23 bound hepcidin-25 (Signal 1), and to a much lesser extent hepcidin-20 (Signal 2). The anti-hepcidin selective Mab 3.23 did not appear to bind detectable levels of hepcidin-22 (MW 2436 Da) or hepcidin-24 (MW 2674 Da).

Experiments performed using MALDI-TOF spectrometry essentially as described immediately above showed that Mab 3.23 bound hepcidin-25 and, to a much lesser extent, hepcidin-20 (FIGS. 1 and 2). The Mab 3.23 did not appear to bind detectable levels of hepcidin-22 (MW 2436 Da), hepcidin-24 (MW 2674 Da), or pro-hepcidin (MW 6929 Da), assuming, of course, that the sera samples tested also contained the expected amounts of these forms of human hepcidin.

Figure 3:
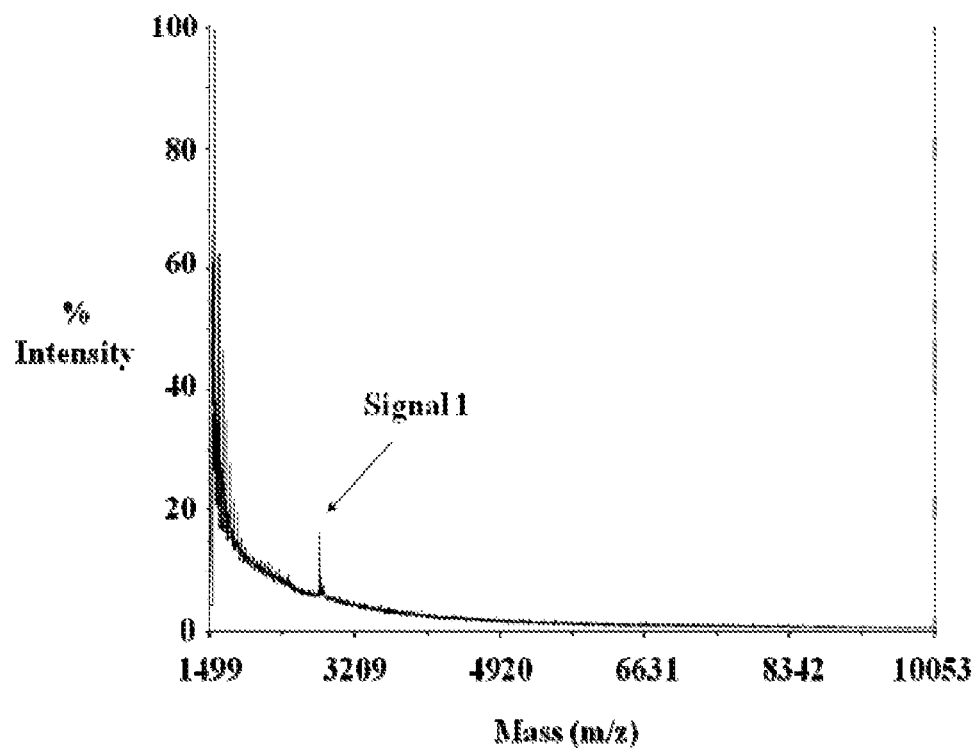
FIG. 3 depicts a MALDI-TOF mass spectrum of the forms of human hepcidin immunoprecipitated from human sera with the anti-hepcidin-25 selective Mab 5E8. Signal 1 has a mass which is consistent with the expected mass of intact human hepcidin-25 (2790 Da). As the chromatogram demonstrates, the anti-hepcidin-25 Mab 5E8 bound detectable amounts of hepcidin-25 only. The mass spectrum was generated on a MALDI-TOF mass spectrometer utilizing a positive ion, linear mode method with a-cyano-4-hydroxycinnamic acid (peptide matrix) as sample matrix essentially as described in Example 6 below.
Figure 4:
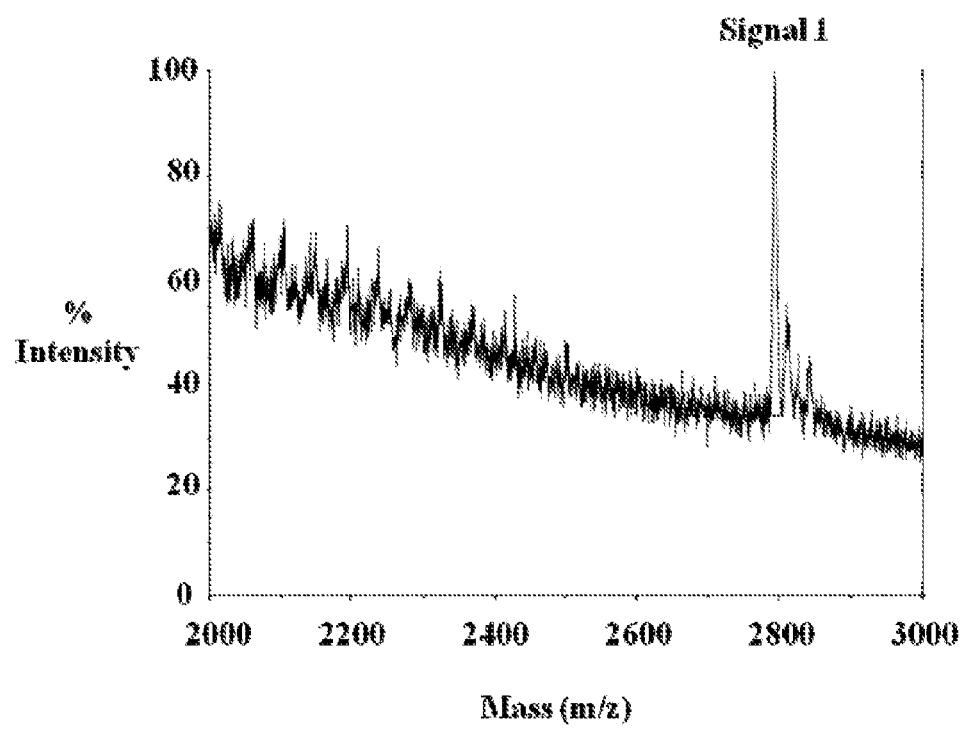
FIG. 4 depicts a magnified view of the mass spectrum shown in FIG. 1 in a relevant region (MW 2000-3000 Da). As the chromatogram demonstrates, the Mab 5E8 bound detectable amounts of hepcidin-25 (Signal 1). The Mab 5E8 did not bind detectable levels of hepcidin-20 (MW of 2192 Da), hepcidin-22 (MW 2436 Da), hepcidin-24 (MW 2674 Da), or pro-hepcidin (MW 6929 Da).

Similar experiments were performed using MALDI-TOF spectrometry to determine which hepcidin species in human serum are bound by Mab 5E8. These experiments determined that Mab 5E8 bound only hepcidin-25 in human serum (FIGS. 3 and 4). Importantly, no hepcidin-20, hepcidin-22, pro-hepcidin, or other hepcidin species were bound Mab 5E8, again, assuming these species of human hepcidin were present in the serum samples as expected.

Thus, immunoassays using the Mab 5E8, or antibodies derived therefrom or related thereto, including, but not limited to Mab OH4, are highly specific and selective for human hepcidin-25, the active, physiologically relevant form of hepcidin in human serum. Further improvement in specificity and/or selectivity is to be expected in immunoassays for human hepcidin-25 that combine the use of the Mab 5E8, or antibodies derived therefrom or related thereto, including, but not limited to Mab OH4, and Mab 3.23, Mab 3.12, or antibodies derived therefrom or related thereto.

Example 7

Sandwich ELISA Assay for Measuring Human Hepcidin-25 (Without Direct Labeling of Antibodies)

A sandwich ELISA is performed as in Example 5, except that i) the labeled conjugate antibody is substituted with unlabeled OH4 and ii) the binding of the OH4 is detected indirectly by the use of a horse radish peroxidase conjugated goat anti-mouse antibody.

Using Mab 3.23 and unlabeled Mab OH4 in a sandwich ELISA as described above, human hepcidin-25 was selectively detected in human serum with a sensitivity of about 0.2 ng/mL.

Example 8

Meso Scale Discovery Sandwich Immunoassay for Measuring Human Hepcidin-25

A human hepcidin-25 Meso Scale Discovery (Meso Scale Discovery, Gaithersburg, Md.) (MSD) immunoassay was constructed using the reagents described above. Briefly, 1 mg of Mab OH4 was biotinylated using a commercially available kit (Pierce Biotechnology, Rockville, Ill.) diluted in 50% glycerol and stored at −20° C. until needed. Streptavidin-coated and blocked wells of an ELISA plate were incubated for 1 hour with biotinylated Mab OH4 at a concentration of 2 mg/L. Afterward, wells were aspirated and washed three times with TBST (Tris buffered saline containing 10 mmol/L Tris pH 7.40, 150 mmol/L NaCl with 1 mL Tween 20/L). Next, 100 µL of hepcidin standards (varying concentrations of synthesized hepcidin-25 protein in assay buffer consisting of 50 mmol/L HEPES, pH 7.40, 150 mmol/L NaCl, 10 mL/L Triton X-100, 5 mmol/L EDTA, and 5 mmol/L EGTA) were added to the wells to generate a calibration curve. At the same time, serum samples were diluted 1:20 in assay buffer and added to their respective wells, and the ELISA plate was allowed to incubate for 1 hour at room temperature. Following aspiration, wells were washed three times with TBST, and 100 µL of a 1:1000 dilution of ruthenium-labeled Mab 3.23 at 1 mg/ml were added to the wells for a 1-hour incubation at room temperature. Following aspiration, wells were washed three times with TBST, and the ELISA plate was developed using a MSD reader, which passed a voltage across the wells and recorded ruthenium electrochemiluminescence from each well. MSD software and SigmaPlot version 8.0 were used for fitting of the calibration curves for the ELISA.

Figure 5:
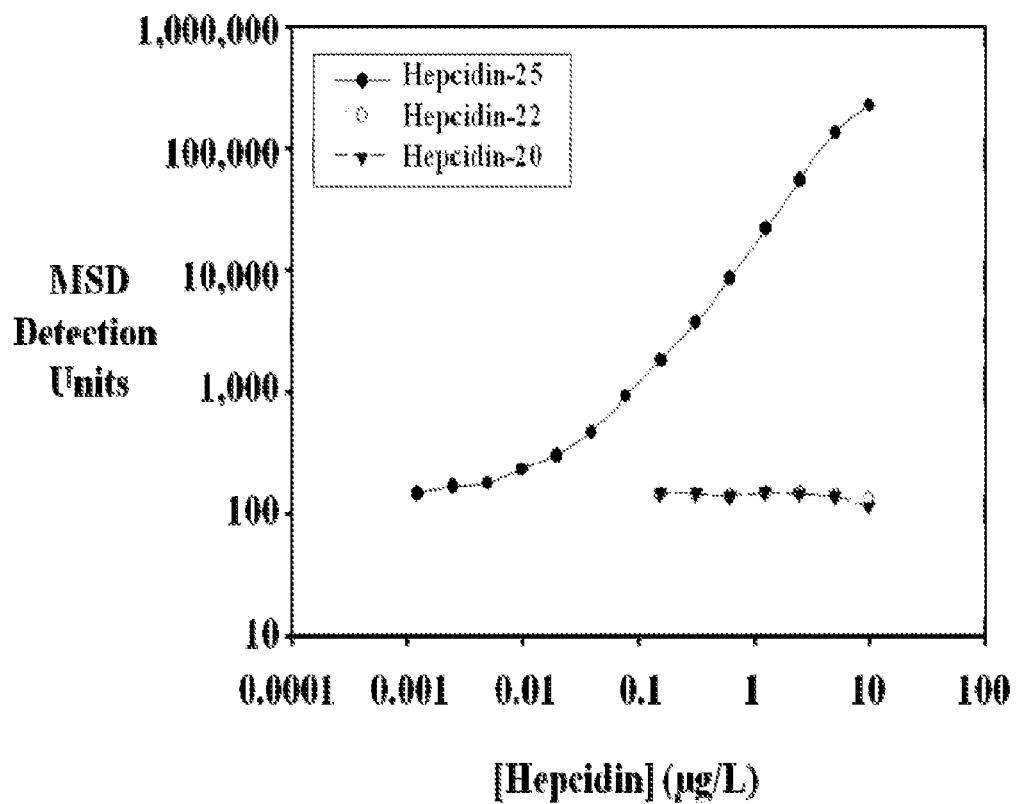
FIG. 5 shows a graph of a calibration curve for hepcidin-25 generated by serially diluting synthesized hepcidin-25 (solid circles) starting at a concentration of 10 μg/L (10 ng/mL) and conducting the MSD immunoassay described in Example 8. The MSD immunoassay was specific for hepcidin-25 and did not recognize hepcidin-20 (solid triangles) or hepcidin-22 (open circles).

The optimal pairing of antibodies in the MSD sandwich immunoassay was determined to be pairing Mab OH4 as the capture antibody and Mab 3.23 as the conjugate antibody. Synthesized hepcidin-25 protein was prepared at a concentration of 10 µg/L and serially diluted to create a standard curve. As FIG. 5 indicates, the ELISA was found to have acceptable dynamic range, background, and sensitivity. Based on a three standard deviation evaluation from the zero calibrator, the sensitivity of the immunoassay was determined to be better than 0.01 µg/L, indicating that the immunoassay should have more than adequate sensitivity to measure human serum hepcidin-25 levels, based on previous estimates of human serum hepcidin-25 levels as measured by LC/MS type assays (Murphy, et al., (2007)). The data graphed in FIG. 2 also indicates that the MSD sandwich immunoassay is selective for hepcidin-25 as it did not detect hepcidin-20 or hepcidin-22. In addition, immunoassay dilution curves for the recombinant standard and actual human serum samples were determined to be parallel, and the immunoassay demonstrated excellent dilutional linearity for human serum samples (data not shown).

The selectivity and sensitivity of the MSD sandwich immunoassay method was compared to a previously described gold standard LC/MS assay (Murphy, et al., (2007)). More specifically, fifty-two (52) human serum samples from a mixture of normal subjects and cancer patients were analyzed using both the MSD sandwich immunoassay, as well as the previously described LC/MS assay shown to be specific for hepcidin-25 (Murphy, et al., (2007)). The results from this comparison showed that the hepcidin-25 values determined by using the MSD immunoassay were very highly correlated with LC/MS hepcidin-25 assay values ($r=0.98$, $p<0.00001$), confirming that the MSD sandwich immunoassay specifically and selectively measures hepcidin-25 in human serum samples (data not shown).

Several parameters of the MSD sandwich immunoassay were evaluated using human serum samples. More specifically, freeze-thaw stability was evaluated by testing four different serum samples. These results showed that the MSD sandwich immunoassay possesses freeze-thaw stability with consistent 80-120% hepcidin-25 recovery even after 5 freeze-thaw cycles. Individual results for the freeze-thaw cycles were as follows: sample A—0.16, 0.16, 0.17, 0.17, 0.17, and 0.17 µg/L respectively; sample B—4.5, 4.4, 4.6, 4.6, 4.6, and 4.4 µg/L respectively; sample C—8.9, 9.6, 9.7, 9.7, 9.9, and 9.6 µg/L, respectively; and sample D—15.1, 15.1, 15.4, 15.7, 15.4 and 15.4 µg/L respectively. The precision of the MSD sandwich immunoassay was assessed using human serum samples containing 0.16, 4.5, and 15.1 µg/L of endogenous hepcidin-25. Intra-assay (n=20) precision results (CVs) were 3.4%, 4.5%, and 3.5%, respectively at the above levels, indicating acceptable precision at all concentrations of hepcidin-25 tested.

To assess the recovery of synthesized hepcidin-25 protein added into human serum, synthesized hepcidin-25 protein was added to four different human serum samples (each containing very low concentrations of endogenous hepcidin-25), at concentrations of 250, 25, 2.5, and 0.25 µg/L respectively. These samples were analyzed using the MSD sandwich immunoassay. Mean (SD) results were 287 (6) µg/L, 24.2 (0.2) µg/L, 2.0 (0.1) µg/L, and 0.23 (0.01) µg/L, respectively, indicating 80-120% recovery at all levels of hepcidin-25 tested.

The normal range of the MSD sandwich immunoassay was established by running 100 serum samples from normal healthy volunteers (50 males and 50 females). The values of hepcidin-25 in these samples ranged from <0.02 µg/L to 25 µg/L, with a mean value of 3.0±0.5 µg/L, consistent with the levels of hepcidin-25 previously reported in normal humans using LC/MS assays (see, Murphy, et al., Blood, 110:1048-54 (2007)).

Interestingly, hepcidin-25 levels in normal human subjects were found to be significantly ($p<0.01$) lower in females (1.8±0.4 µg/L) compared to males (4.2±0.8 µg/L). Hepcidin-25 levels in these normal subjects were also compared to serum ferritin concentrations and were found to be directly correlated with serum ferritin levels ($r=0.71$, $p<0.001$)(data not shown).

Finally, hepcidin-25 levels in the serum of cancer patients (n=34) were compared to hepcidin-25 levels in the serum of normal healthy volunteers (n=100), each determined by the MSD sandwich immunoassay. The results of this comparison demonstrated that hepcidin-25 levels are significantly ($p<0.001$) elevated in patients with cancer (70.9±10.4 µg/L) compared to normal controls (3.0±0.5 µg/L) (data not shown). Interestingly, patient cohorts with both hematological (83.3±11.9 µg/L) and non-hematological malignancies (58.4±17 µg/L) each demonstrated significantly increased hepcidin-25 levels compared to normal controls ($p<0.001$ for both), suggesting that elevated hepcidin-25 levels may play an important role in cancer-associated anemia (data not shown).

Compared to existing ELISA methods, which are not specific for hepcidin-25 and may cross-react with pro-hepcidin and other non-relevant hepcidin species, the MSD sandwich immunoassay described here specifically and selectively measures hepcidin-25 levels in human serum and correlates well with a previously described gold-standard method LC/MS assay for hepcidin-25. One advantage of the MSD sandwich immunoassay over an LC/MS type method for measuring human serum hepcidin levels is that the MSD sandwich immunoassay can be implemented in most clinical laboratories, which usually have neither the complex equipment nor the highly specialized operator expertise required to routinely perform LC/MS type assays. In addition, the MSD sandwich immunoassay should have the potential for much higher throughput than an LC/MS assay. Therefore, the MSD sandwich immunoassay provides a method that can be routinely utilized clinically to selectively measure hepcidin-25 levels in human subjects.

We claim:

1. A monoclonal antibody comprising six complementarity determining regions (CDRs) selected from the group consisting of:
   (i) LCDR1, LCDR2, LCDR3, HCDR1, HCDR2, and HCDR3 having the amino acid sequences as shown in SEQ ID NOs: 20, 21, 22, 42, 43, and 44, respectively;
   (ii) LCDR1, LCDR2, LCDR3, HCDR1, HCDR2, and HCDR3 having the amino acid sequences as shown in SEQ ID NOs: 20, 21, 23, 42, 43 and 44, respectively;
   (iii) LCDR1, LCDR2, LCDR3, HCDR1, HCDR2, and HCDR3 having the amino acid sequences as shown in SEQ ID NOs: 24, 25, 23, 42, 43 and 44, respectively;
   (iv) LCDR1, LCDR2, LCDR3, HCDR1, HCDR2, and HCDR3 having the amino acid sequences as shown in SEQ ID NOs: 26, 25, 27, 42, 43 and 44, respectively;
   (v) LCDR1, LCDR2, LCDR3, HCDR1, HCDR2, and HCDR3 having the amino acid sequences as shown in SEQ ID NOs: 26, 25, 28, 42, 43 and 44, respectively; and
   (vi) LCDR1, LCDR2, LCDR3, HCDR1, HCDR2, and HCDR3 having the amino acid sequences as shown in SEQ ID NOs: 17, 18, 19, 42, 43, and 44, respectively, and wherein the antibody binds human hepcidin-25.

2. The antibody of claim 1 that comprises a light chain variable region (LCVR) polypeptide and a heavy chain variable region (HCVR) polypeptide wherein:
   (i) the LCVR and the HCVR polypeptides have the amino acid sequences as shown in SEQ ID NOs: 59 and 58 respectively;
   (ii) the LCVR and the HCVR polypeptides have the amino acid sequences as shown in SEQ ID NOs: 60 and 58, respectively;
   (iii) the LCVR and the HCVR polypeptides have the amino acid sequences as shown in SEQ ID NOs: 61 and 58, respectively;
   (iv) the LCVR and the HCVR polypeptides have the amino acid sequences as shown in SEQ ID NOs: 62 and 58, respectively;
   (v) the LCVR and the HCVR have the amino acid sequences as shown in SEQ ID NOs: 63 and 58, respectively; or
   (vi) the LCVR and the HCVR have the amino acid sequences as shown in SEQ ID NOs: 57 and 58, respectively.

3. The antibody of claim 2 comprising a heavy chain and a light chain having (i) the amino acid sequences as shown in SEQ ID NOs: 76 and 77, respectively; (ii) the amino acid sequences as shown in SEQ ID NOs: 76 and 78, respectively; (iii) amino acid sequences as shown in SEQ ID NOs: 76 and 79, respectively; (iv) the amino acid sequences as shown in SEQ ID NOs: 76 and 80, respectively; or (v) amino acid sequences as shown in SEQ ID NOs: 76 and 81, respectively.

4. A method of increasing serum iron levels, reticulocyte count, red blood cell count, hemoglobin, and/or hematocrit comprising administering to a human subject an effective amount of the antibody of claim 1.

5. A method of treating anemia in a human subject in need thereof, comprising administering to the human subject an effective amount of the antibody of claim 1.

6. A method for measuring the amount of human hepcidin-25 in a sample of tissue or biological fluid, said method comprising the steps of:
   (i) obtaining the sample of tissue or biological fluid;
   (ii) causing the sample to contact the antibody of claim 1; and
   (iii) detecting the amount of human hepcidin-25 bound to the antibody in said sample quantitatively, semi-quantitatively or qualitatively.

7. A method for quantifying the amount of human hepcidin-25 protein in a sample of tissue or biological fluid comprising the steps of:
   (i) coating a solid support with (a) a first antibody according to claim 1, or (b) a first antibody that binds an epitope contained within amino acids 5 to 25, inclusive, of SEQ ID NO:1;
   (ii) applying the sample to said antibody coated solid support;
   (iii) removing unbound sample;
   (iv) if the first antibody in step (i) is (a), applying to the solid support a second antibody that binds an epitope contained within amino acids 5 to 25, inclusive, of SEQ ID NO:1, or, if the first antibody in step (i) is (b), applying to the solid support a second antibody according to claim 1;
   (v) removing unbound second antibody; and
   (vi) detecting the amount of human hepcidin-25 bound to the second antibody in said sample quantitatively, semi-quantitatively or qualitatively.

8. The method of claim 7 wherein the first or second antibody comprises a light chain and a heavy chain having the amino acid sequences as shown in SEQ ID NOs: 84 and 85, respectively.

9. The method of claim 7 wherein the first or second antibody comprises a light chain and a heavy chain having the amino acid sequences as shown in SEQ ID NOs: 82 and 83, respectively.

10. The method according to claim 8 wherein said sample is blood, plasma, serum, urine, cerebro-spinal fluid (CSF), amniotic fluid, saliva, sweat, ascite fluid, lymph, cyst fluid, breast milk, wound fluid, or derived there from, and wherein said sample contacts said antibody in an enzyme immunoassay (EIA), ELISA, a sandwich ELISA assay, radioimmunoassay, a precipitation reaction or a fluorescent immunoassay.

11. The method according to claim 9 wherein said sample is blood, plasma, serum, urine, cerebro-spinal fluid (CSF), amniotic fluid, saliva, sweat, ascite fluid, lymph, cyst fluid, breast milk, wound fluid, or derived there from, and wherein said sample contacts said antibody in an enzyme immunoassay (EIA), ELISA, a sandwich ELISA assay, radioimmunoassay, a precipitation reaction or a fluorescent immunoassay.

12. The method of claim 10 wherein only the first or the second antibody is labeled with a detectable moiety.

13. The method of claim 11 wherein only the first or the second antibody is labeled with a detectable moiety.

14. The method of claim 13 wherein said detection is indirect.

15. A kit for detecting or quantifying human hepcidin-25 comprising the antibody of claim 1.

16. A kit for detecting or quantifying human hepcidin-25 comprising the antibody of claim 2.

17. A kit for detecting or quantifying human hepcidin-25 comprising the antibody of claim 3.

* * * * *